(12) United States Patent
Mahoney et al.

(10) Patent No.: US 10,106,496 B2
(45) Date of Patent: Oct. 23, 2018

(54) HYDROXY METHIONINE ANALOG FORMULATIONS SUITABLE FOR SPECIALTY CHEMICAL APPLICATIONS

(71) Applicant: Novus International Inc., St. Charles, MO (US)

(72) Inventors: Matthew Mahoney, St. Charles, MO (US); Graciela Arhancet, St. Charles, MO (US); Xiaojun Wang, St. Charles, MO (US); Tracy Rode, St. Charles, MO (US); Scott Long, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 15/628,872

(22) Filed: Jun. 21, 2017

(65) Prior Publication Data

US 2017/0369434 A1    Dec. 28, 2017

Related U.S. Application Data

(60) Provisional application No. 62/354,323, filed on Jun. 24, 2016.

(51) Int. Cl.
| | |
|---|---|
| *C07C 323/52* | (2006.01) |
| *C07C 323/14* | (2006.01) |
| *C07C 59/01* | (2006.01) |
| *C07C 31/02* | (2006.01) |
| *C07C 9/00* | (2006.01) |

(52) U.S. Cl.
CPC ............. *C07C 323/52* (2013.01); *C07C 9/00* (2013.01); *C07C 31/02* (2013.01); *C07C 59/01* (2013.01); *C07C 323/14* (2013.01)

(58) Field of Classification Search
CPC .......................... C07C 323/52; C07C 323/14
See application file for complete search history.

(56) References Cited

U.S. PATENT DOCUMENTS

| | | |
|---|---|---|
| 4,419,198 A | 12/1983 | Breda |
| 4,524,077 A | 6/1985 | Ruest |
| 6,008,409 A | 12/1999 | Hasseberg |
| 6,627,773 B1 * | 9/2003 | Ikudome ............... C07C 319/20 562/526 |
| 6,743,946 B1 | 6/2004 | Carencotte |
| 2006/0287543 A1 | 12/2006 | Trehy |
| 2009/0318715 A1 | 12/2009 | Deck |

FOREIGN PATENT DOCUMENTS

| | | |
|---|---|---|
| JP | 2007238552 A | 9/2017 |
| WO | 2007030409 A2 | 3/2007 |

OTHER PUBLICATIONS

International Search Report and Written Opinion dated Sep. 13, 2017 in related International application No. PCT/US17/38492, 9 pp.

* cited by examiner

*Primary Examiner* — Paul A Zucker
(74) *Attorney, Agent, or Firm* — Polsinelli PC

(57) ABSTRACT

Formulations comprising hydroxy methionine analog and having low levels of sulfate ions and bisulfate salts, processes for preparing the formulations, compositions comprising the formulations, and methods of using the formulations.

24 Claims, 2 Drawing Sheets

HYDROXY METHIONINE ANALOG FORMULATIONS SUITABLE FOR SPECIALTY CHEMICAL APPLICATIONS

CROSS-REFERENCE TO RELATED APPLICATIONS

This application claims the benefit of U.S. Provisional Application No. 62/354,323, filed Jun. 24, 2016, which is hereby incorporated by reference in its entirety.

FIELD OF THE INVENTION

The present disclosure generally relates to hydroxy methionine analog formulations with low levels of sulfate and bisulfate ions and improved color and odor. Accordingly the formulations are suitable for specialty chemical applications.

BACKGROUND OF THE INVENTION

Hydroxy methionine analogs such as 2-hydroxy-4-(methylthio)butanoic acid (HMTBA) are widely used as feed additives for livestock. HMTBA generally is manufactured as a dark liquid with a sulfurous odor containing at least about 88% HMTBA free acid, up to about 12% water, and about 0.5-3% of ammonium bisulfate, as well as other minor impurities. The chemical functionality of HMTBA makes it a suitable building block for many materials in many more applications and recently there has been a renewed interest in the use of HMTBA for specialty chemicals, such as polymers, surfactants, solvents, etc. All these specialty applications require well-defined specifications regarding color, odor, shelf life for the final product and, thus, for HMTBA as a component or raw material. Ammonium bisulfate while it is a known antibacterial agent or acidifier in feed contributes to undesired generation of color and odor in specialty chemical applications. Therefore, there is a need for thermally stable HMTBA formulations with minimal color and odor for specialty chemical uses.

SUMMARY OF THE INVENTION

Among the various aspects of the present disclosure is the provision of a formulation comprising compounds of Formula (I), about 15% or less by weight of water, and less than about 2700 ppm by weight of sulfate ion, wherein k is 1 in less than 85% of compounds of Formula (I):

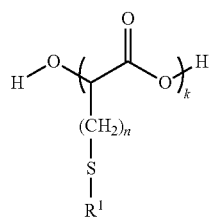

wherein:
R¹ is alkyl or substituted alkyl;
k is an integer from 1 to 1000; and
n is an integer from 1 to 20.

Another aspect of the present disclosure encompasses a formulation comprising compounds of Formula (I), about 15% or less by weight of water, and having an American Public Health Association (APHA) color value of 200 or less, wherein k is 1 in less than 85% of the compounds of Formula (I): the compounds of Formula (I):

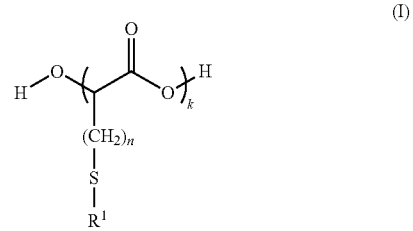

wherein:
R¹ is alkyl or substituted alkyl;
k is an integer from 1 to 1000; and
n is an integer from 1 to 20.

A further aspect of the present disclosure provides a process for preparing the formulations described above from a feed grade formulation comprising compounds of Formula (I), sulfate ions, bisulfate ions, and color bodies. The process comprises (a) contacting an aqueous solution of the feed grade formulation comprising compounds of Formula (I) with an adsorbent to remove color bodies, thereby producing a decolorized aqueous solution; (b) extracting the decolorized aqueous solution with a solvent having limited water miscibility to form an organic phase comprising the solvent having limited water miscibility and compounds of Formula (I) and an aqueous phase comprising sulfate ions and bisulfate salts; and (c) removing the solvent from the organic phase to form the formulation.

Still another aspect of the present disclosure encompasses a process for preparing the formulations described above from a feed grade formulation comprising compounds of Formula (I), sulfate ions, bisulfate ions, and color bodies. The process comprises (a) contacting an aqueous solution of the feed grade formulation comprising compounds of Formula (I) with an adsorbent to remove color bodies, thereby producing a decolorized aqueous solution; (b) contacting the decolorized aqueous solution with at least one ion exchange resin to remove sulfate ions and bisulfate salts and form an aqueous elute; and (c) removing water from the aqueous eluate to form the formulation.

Other features and iterations of the invention are described in more detail below.

DETAILED DESCRIPTION OF THE INVENTION

Figure 1:
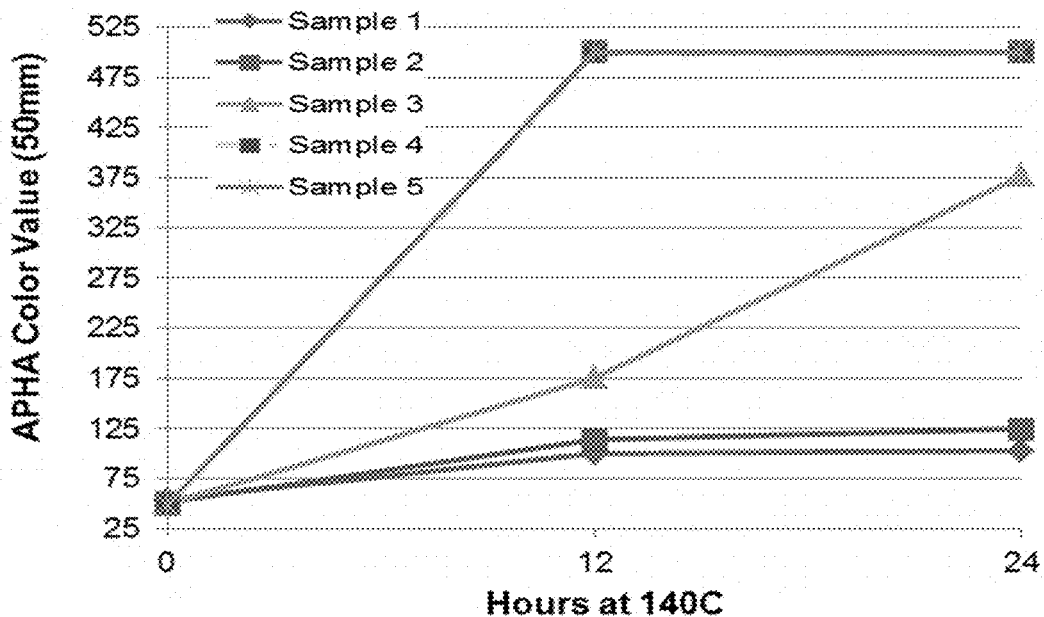
FIG. 1 illustrates APHA color value changes over time in HMTBA samples with added sulfuric acid and heated to 140° C. Plotted is the APHA color value as a function of hours at 140° C.

The present disclosure provides formulations of hydroxy methionine analogs that have low levels of sulfate ions, bisulfate ions, and color bodies. Because of the low levels of sulfate and bisulfate ions, the formulations disclosed herein are chemically stable at elevated temperatures. i.e., they do not become colored or odorous. Accordingly, the hydroxy methionine analog formulations disclosed herein are suitable for specialty chemical applications. Also provided are processes for preparing the formulations disclosed herein, wherein the processes comprise removing sulfate ions, bisulfate ions, and color bodies from feed grade formulations of hydroxy methionine analog. Also provided herein are compositions comprising the formulations disclosed herein, as well as processes for preparing derivatives of the hydroxy methionine analogs the using the formulations disclosed herein as the starting material.

(I) Formulations

One aspect of the present disclosure provides hydroxy methionine analog formulations with low levels of sulfate ions, bisulfate ions, and color bodies such that the formulations are suitable for specialty chemical applications. In particular, the formulations disclosed herein comprise compounds of Formula (I), as detailed below, about 15% or less by weight of water, about 2700 ppm or less by weight of sulfate ion, about 500 ppm or less by weight of bisulfate ion, and have a pH of at least 1.3 at 15% water content. Accordingly, the formulations are substantially free of color bodies and volatile odorous compounds. Moreover, the formulations are stable under elevated temperatures.

(a) Components of the Formulation (i) Compounds of Formula (I)

The formulations disclosed herein comprise compounds of Formula (I):

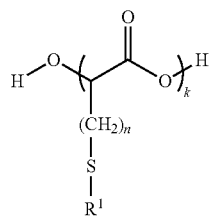

wherein:
$R^1$ is alkyl or substituted alkyl;
k is an integer of 1 or greater; and
n is an integer of 1 or greater.

In some embodiments, $R^1$ may be $C_1$ to $C_6$ alkyl or $C_1$ to $C_6$ substituted alkyl. In further embodiments, $R^1$ may be methyl, ethyl, propyl, isopropyl, butyl, tert-butyl, hexyl, cyclohexyl, and the like. In specific embodiments, $R^1$ may be methyl.

In certain embodiments, n may range from 1 to 20 or from 1 to 10. In other embodiments, n may be 1, 2, 3, 4, or 5. In specific embodiments, n may be 1 or 2.

In general, k may range from 1 to about 1000. For example, k may range from 1 to about 500, from 1 to about 250, from 1 to about 100, from 1 to about 50, from 1 to about 20, from 1 to about 10, from 1 to 5, from 1 to 4, or from 1 to 3. In some embodiments, k may be the same in every compound of the formulation (e.g., k may be 1, k may be 2, etc.). In other embodiments, k may differ between the compounds of the formulation (e.g., k may be 1-4, 1-10, 1-20, and so forth). Stated another way, the formulation comprises a mixture of monomer, dimers, trimers, tetramers, and longer oligomers.

In some embodiments, the percentage of monomers (i.e., k=1) in the formulation may vary. For example, the percentage of monomers may be about 99.9% or less, may be about 99% or less, maybe about 95% or less, may be about 90% or less, may be about 85% or less, may be about 80% or less, may be about 75% or less, may be about 70% or less, may be about 60% or less, may be about 50% or less, may be about 40% or less, may be about 30% or less, may be about 20% or less, may be about 10% or less, or may be about 5% or less by weight. In specific embodiments, the percentage of monomers may be about 85% or less by weight.

In specific embodiments, $R^1$ may be methyl and n may be 2.

The compounds of Formula (I) may have at least one chiral center, as denoted with an asterisk in the schematic below:

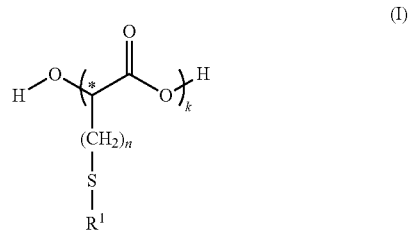

wherein $R^1$, k, and n are as defined above. Each chiral center may have an R or an S configuration. In compounds comprising one chiral carbon, the configuration may be R or S. In compounds comprising two or more chiral carbons, the configuration of each will be independently R or S. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, and so forth.

The concentration of compounds of Formula (I) in the formulation can and will vary depending, for example, on the concentration of water in the formulation. In various embodiments, the formulation comprises at least about 50%, at least about 55%, at least about 60%, at least about 65%, at least about 70%, at least about 75%, at least about 80%, at least about 85%, at least about 90%, at least about 92%, at least about 95%, at least about 96%, at least about 97%, about at least about 98%, at least about 99%, at least about 99.5%, or at least about 99.9% by weight of compounds of Formula (I).

(ii) Water

Another component of the formulation is water. In general, the amount of water present in the formulation is about 15% or less by weight. In some embodiments, the formulation comprises about 10% or less of water by weight. In other embodiments, the formulation comprises about 5% or less of water by weight. In still further embodiments, the formulation comprises about 4% or less, about 3% or less, about 2% or less, about 1% or less of water by weight. In some embodiments, the water content of the formulation may be about 15% by weight. In other embodiments, the water content of the formulation may be about 5% by weight.

(iii) Sulfate Ion

The formulation also comprises sulfate ions, which are derived from sulfuric acid used in the manufacture of compounds of Formula (I). In general, the formulation comprises about 2700 ppm or less by weight of sulfate ion. In certain embodiments, the formulation comprises about 2500 ppm or less, about 2000 ppm or less, about 1500 ppm or less, about 1000 ppm or less, about 500 ppm or less, about 100 ppm or less, about 50 ppm or less, or about 10 ppm or less of sulfate ion by weight. In some embodiments, the formulation comprises at least 1 ppm of sulfate ion by weight. For example, the formulation may comprise from 1 to about 2700 ppm, from 1 to about 2000 ppm, from 1 to about 1500 ppm, from 1 to about 1000 ppm, or from 1 to about 500 ppm of sulfate ion by weight.

(iv) Bisulfate Ion

The formulation also comprises bisulfate ($HSO_4^-$) ions, which may be derived from ammonium bisulfate used in the manufacturing process. In general, the formulation comprises about 500 ppm or less by weight of bisulfate ion. In various embodiments, the formulation comprises about 400 ppm or less, about 300 ppm or less, about 200 ppm or less, about 100 ppm or less, about 50 ppm or less, or about 10 ppm or less by weight of bisulfate ion. In certain embodiments, the formulation comprises at least 1 ppm by weight of bisulfate ion. For example, the formulation may comprise from 1 to about 500 ppm, from 1 to about of 200 by weight of bisulfate ion.

(v) Exemplary Formulations

In one embodiment, the formulation comprises compounds of Formula (I) in which $R^1$ is methyl, n is 2, and k is 1, and the formulation further comprises about 15% or less by weight of water, about 2700 ppm or less by weight of sulfate ion, about 500 ppm or less by weight of bisulfate ion, and has a pH of at least 1.3 at a water content of 15%.

(b) Properties of the Formulation

The formulations detailed above comprise low levels of sulfate and bisulfate ions. Accordingly, the formulations have pH values of at least 1.3 at 15% water content. In certain embodiments, the pH of the formulation may range from about 1.3 to about 1.4, from about 1.4 to about 1.5, from about 1.5 to about 1.6, from 1.6, to about 1.7, from about 1.7 to about 1.8, or greater than about 1.8 at a water content of 15%

Because of the low levels of sulfate and bisulfate ions, the formulations described herein maintain minimal color under storage conditions and do not impart dark color to products when reacted under temperatures <140° C. for less than 12 hours. Stated another way, the formulations have low levels of color bodies or colored impurities. The color of the formulations can be measured using a spectrophotometric colorimeter and converted to a color value using a standard color scale. In some embodiments, the color scale can be the American Public Health Association (APHA) color scale, which is also called a "yellowness index." The APHA color scale ranges from 0 (distilled water) to 500 (pale yellow) and is used to differentiate small amounts of yellowness in near "water-white" liquids. In other embodiments, the color scale can be the Gardner color scale. The Gardner Color scale ranges from 0 (distilled water) to 1 (light yellow), then continues to a dark, murky 18. Over the 0 to 18 range, there is an increase in yellowness and decrease in lightness.

In general, the formulations disclosed herein have APHA color values of 200 or less. In some embodiments, the APHA color value may be about 150 or less, about 100 or less, or about 50 or less at water content of 0.5-3%. In contrast, feed grade formulations of the compounds of Formula (I) (e.g., HMTBA animal supplement) generally have APHA color values that are off scale (i.e., >500).

Because of the low levels of sulfate ions and bisulfate salts, the formulations described herein have thermal stability that is compatible with specialty applications. In some embodiments, the formulations disclosed herein can be heated to a temperature of about 140° C. for up to about 12 hours with no appreciable change in the APHA color values. In other embodiments, the formulations disclosed herein may have APHA color values of 300 or less after being heated to about 140° C. for up to about 12 hours. In still other embodiments, the formulations disclosed herein may have APHA color values of 400 or less after being heated to about 140° C. for up to about 12 hours. In yet additional embodiments, the formulations disclosed herein may have APHA color values of 500 or less after being heated to about 140° C. for up to about 12 hours.

The formulations disclosed herein also have low levels of odorous compounds. In general, the odorous compounds present in the formulations are sulfur containing compounds such as methyl mercaptan, dimethyl sulfide, allyl methyl sulfide, and dimethyl disulfide. The level of the odorous compounds may be about 10 ppm or less, or about 5 ppm or less by weight.

(II) Processes for Preparing the Specialty Formulations

Still another aspect of the present disclosure encompasses processes for preparing the specialty formulations described above in section (I). In particular, the formulations disclosed herein are prepared from feed grade formulations comprising compounds of Formula (I), wherein the feed grade formulations further comprise sulfate ions, bisulfate ions, and color bodies. In general, the feed grade formulations comprise about 88% by weight of compounds of Formula (I) and about 12% by weight of water. One process comprises removing color bodies from an aqueous solution of a feed grade formulation comprising compounds of Formula (I) by contact with an absorbent, and then removing the sulfate and bisulfate ions by solvent extraction. Another process comprise removing color bodies from an aqueous solution of a feed grade formulation comprising compounds of Formula (I) by contact with an absorbent, and then removing the sulfate and bisulfate ions by ion exchange. Those skilled in the art readily appreciate that the order of operations in the process can be modified.

(a) Solvent Extraction Process

One process for preparing the formulations disclosed herein comprises contacting an aqueous solution of a feed grade formulation comprising compounds of Formula (I) with an absorbent to remove color bodies, thereby producing a decolorized aqueous solution. The process further comprises extracting the decolorized aqueous solution with a solvent having limited water miscibility such that two phases are formed, an organic phase comprising the solvent and compounds of Formula (I) and an aqueous phase comprising sulfate and bisulfate ions. The last step of the process comprises removing the solvent from the organic phase to prepare the formulation detailed in section (I).

(i) Aqueous Solution of the Feed Grade Formulation

The feed grade formulation comprising compounds of Formula (I) also comprises sulfate ions, bisulfate ions, and color bodies. An aqueous solution of the feed grade formulation comprising compounds of Formula (I) may prepared by diluting the feed grade formulation with water. The feed grade composition may also be diluted with a mixture of water and a polar solvent to form the aqueous solution of the feed grade formulation comprising compounds of Formula (I). Examples of suitable polar solvents to be mixed with water include, without limit, acetamide, acetic acid, acetone, acetonitrile, dimethylacetamide, dimethylformamide, dimethyl sulfoxide, dioxane, ethanol, formamide, formic acid, methanol, n-propanol, isopropanol, propylene glycol, tetrahydrofuran, or combinations thereof. The amount of polar solvent present in the mixture of water and polar solvent may range from about 1% to about 99% by weight.

The amount of water (or mixture of water and polar solvent) used to prepare the aqueous solution of the feed grade formulation comprising compounds of Formula (I) can and will vary depending, for example, on the concentration of the compounds of Formula (I) in the feed grade formulation. In general, the feed grade formulation comprising compounds of Formula (I) is diluted with sufficient water (or mixture of water and polar solvent) such that the aqueous solution of the feed grade formulation comprises about 18% or less by weight of compounds of Formula (I). In specific embodiments, the feed grade formulation is diluted with sufficient water (or mixture of water and polar solvent) such that the aqueous solution of the feed grade formulation comprises about 15% by weight of compounds of Formula (I).

(ii) Optional Filtration Step

In some embodiments, the aqueous solution of the feed grade formulation comprising compounds of Formula (I) may be filtered to remove oily color bodies. The filtration may comprise passing the aqueous solution of the feed grade formulation comprising compounds of Formula (I) through diatomaceous earth (available under the tradename CELITE®), diatomite, perlite, silica, cellulose (e.g., α-cellulose), or other filter aid known in the art.

The aqueous solution of the feed grade formulation comprising compounds of Formula (I) may be filtered immediately after preparation of the aqueous solution. Alternatively, the aqueous solution of the feed grade formulation comprising compounds of Formula (I) may be filtered a period of time after preparation of the aqueous solution. For example, in some embodiments, the aqueous solution of the feed grade formulation comprising compounds of Formula (I) may be allowed to stand for up to about 12 hours and then filtered. In other embodiments, the aqueous solution of the feed grade formulation comprising compounds of Formula (I) may be allowed to stand for about 12 to 18 hours, from about 18 to 24 hours, or from about 24 to 30 hours and then filtered.

(iii) Contact with Adsorbent

The process comprises contacting the aqueous solution comprising compounds of Formula (I) with an adsorbent to remove aqueous color bodies from the aqueous solution, thereby producing a decolorized aqueous solution.

A variety of adsorbents may be used in the process. Non-limiting examples of suitable adsorbents include activated charcoal (also called activated carbon), silica gels, silicates, alumina, zeolite, bentonite, and mineral clays. In specific embodiments, the adsorbent is activated charcoal. Activated carbon is an amorphous solid that has very large internal surface area and pore volume, and has low affinity for water. The activated charcoal may be powdered (or pulverized) or granular (e.g., 4-10 mesh size, 20-40 mesh size, etc.)

The amount of adsorbent that is contacted with the aqueous solution comprising compounds of Formula (I) can and will vary. Generally, weight ratio of the adsorbent to the compounds of Formula (I) may range from about 0.001:1 to about 0.05:1. In embodiments in which the adsorbent is activated charcoal, the weight ratio of activated charcoal to compounds of Formula (I) may range from about 0.005:1 to about 0.01:1.

In some embodiments, contact between the adsorbent and the aqueous solution comprising compounds of Formula (I) may be performed using a batch process. For example, the adsorbent may be added to the aqueous solution comprising compounds of Formula (I) and contact may be facilitated by stirring, shaking, or other form of agitation. The duration of the contact between the adsorbent and the aqueous solution comprising compounds of Formula (I) may range from about 30 minutes to about 48 hours. After the appropriate period of time, the adsorbent may be separated from the decolorized aqueous solution by filtration, centrifugation, or other suitable means. In other embodiments, contact between the adsorbent and the aqueous solution comprising compounds of Formula (I) may proceed via a fixed bed (column) process. For example, the aqueous solution comprising compounds of Formula (I) may be passed through a column containing the adsorbent, wherein color bodies adsorb to the adsorbent and the column flow through is the decolorized aqueous solution. The solution may be passed through the column one time or more than one time.

Contact between the aqueous solution of the feed grade formulation comprising compounds of Formula (I) and the adsorbent may occur at about 20-25° C. (i.e., room temperature). Alternatively, contact may occur at a temperature from about 25-30° C., from about 30-35° C., or from about 35-40° C. In general, contact between the adsorbent and the aqueous solution of the feed grade formulation comprising compounds of Formula (I) occurs at atmospheric pressure.

The adsorbent removes color bodies from the aqueous solution comprising compounds of Formula (I), thereby producing a decolorized aqueous solution comprising compounds of Formula (I). The APHA color value of the decolorized aqueous solution may be reduced at least about 2-fold, at least about 5-fold, at least about 10-fold, at least about 30-fold, or at least about 60-fold relative to the starting aqueous solution of the feed grade formulation comprising compounds of Formula (I).

(iv) Solvent Extraction

The process further comprises contacting the decolorized aqueous solution comprising compounds of Formula (I) with a solvent having limited water miscibility to form two phases, an organic phase comprising the solvent with limited water miscibility and compounds of Formula (I) and an aqueous phase comprising sulfate and bisulfate ions.

A variety of solvents may be used in the process. In general, solvents with limited water miscibility have solubility in water of about 10% w/w or less. Non-limiting examples of solvents having limited water miscibility include benzene, n-butanol, butyl acetate, carbon tetrachloride, chlorobenzene, chloroform, chloromethane, cyclohexane, dichloromethane, 1,2-dichloroethane, di-tert-butyl ether, dimethyl ether, diethylene glycol, diethyl carbamate, diethyl ether, diglyme, diisopropyl ether, ethyl acetate, ethyl tert-butyl ether, ethylene oxide, fluorobenzene, heptane, hexane, methyl isobutyl ketone, methyl tert-butyl ether, pentane, trichloroethylene, toluene, xylene, or combinations thereof. In some embodiments, the solvent with limited water miscibility may be methyl isobutyl ketone, ethyl acetate, or methyl tert-butyl ether.

The amount of solvent contacted with the decolorized aqueous solution comprising compounds of Formula (I) can and will vary depending upon the solvent used and the level of impurities in the decolorized aqueous solution. In general, the weight ratio of the solvent to the compounds of Formula (I) may range from about 0.1:1 to about 15:1. In various embodiments, the weight ratio of the solvent to the compounds of Formula (I) may range from about 0.05:1 to about 10:1, from about 0.1:1 to about 5:1, from about 0.375:1 to about 1.5:1, or from about 0.6:1 to about 0.9:1.

Contact between the decolorized aqueous solution and the limited water-miscible solvent forms a two phase system. Contacting the two phases may be accomplished using liquid-liquid extraction equipment such as a Karr or Scheibel column, a mixer settler, or other suitable continuous contacting equipment known in the art. Batch contacting may be accomplished by mixing the two phase system by inversion, rotation, stirring, shaking, or other means known in the art. After contacting, the system is allowed to separate into two phases, i.e., the organic phase comprising the solvent and compounds of Formula (I) and the aqueous phase comprising sulfate and bisulfate ions. The two phases may be separated using industrial separators, centrifugal separators, decantation, or similar means known in the art.

The solvent extraction may occur at a temperature ranging from about 15° C. to about 80° C. In specific embodiments, the solvent extraction may occur at room temperature.

(v) Removing the Solvent from the Organic Phase

The process further comprises removing the solvent from the organic phase to form the formulations detailed above in section (I). The solvent may be removed from the organic phase by evaporation or distillation. Suitable evaporative means include reduced pressure evaporation, simple effect evaporation, multiple effect evaporation, or other evaporative means.

(b) Ion Exchange Process

Another process for preparing the formulations disclosed herein comprises contacting an aqueous solution of the feed grade formulation comprising compounds of Formula (I) with an adsorbent to remove the color bodies, thereby producing a decolorized aqueous solution. The process further comprises contacting the decolorized aqueous solution with at least one ion exchange resin to form an aqueous elute having low levels of sulfate and bisulfate ions. The last step of the process comprises removing water from the aqueous eluate to form the formulation detailed above in section (I).

(i) Contact with Adsorbent

The process comprises contacting an aqueous solution of the feed grade formulation comprising compounds of Formula (I) with an adsorbent to produce a decolorized aqueous solution. The aqueous solution of the feed grade formulation comprising compounds of Formula (I) is described above in section (II)(a)(i), the optional filtration step is described above in section (II)(a)(ii), and contact with the adsorbent is detailed above in section (II)(a)(iii).

(ii) Contact with Ion Exchange Resin

The next step of the process comprises contacting the decolorized aqueous solution with at least one ion exchange resin, thereby forming an aqueous eluate having low levels of sulfate and bisulfate ions.

Most ion exchange resins are based on crosslinked polystyrene or crosslinked acrylic or methacrylic acid polymers that are modified to contain functional groups. In some embodiments, the ion exchange resin may be a cation exchange resin. Cation exchange resins can be strongly acidic and contain sulfonic acid functional groups, or weakly acidic and contain carboxylic acid functional groups. In other embodiments, the ion exchange resin may be an anion exchange resin. Anion exchange resins can be strongly basic and contain quaternary amino functional groups, or weakly acidic and contain primary, secondary, and/or tertiary amino functional groups.

In general, the process comprises contact with both a cation exchange resin and an anion exchange resin. The cation exchange resin removes ammonium and other cations, and the anion exchange resin removes sulfate, bisulfate, and other anions from the decolorized aqueous solution. In some embodiments, the process comprises contact with the cation exchange resin followed by contact with the anion exchange resin to form the aqueous eluate. In other embodiments, the process comprises contact with the anion exchange resin followed by contact with the cation exchange resin to form the aqueous eluate.

The amount of ion exchange resin that is contacted with the decolorized aqueous solution can and will vary depending upon, for example, the type of functional groups on the resin and the levels of salt impurities in the decolorized aqueous solution. Means for determining the appropriate amount are well-known in the art.

(iii) Removing Water from the Aqueous Eluate

The process further comprises removing water from the aqueous eluate to form the formulation detailed above in section (I). The water (or mixture of water and polar solvent) may be removed from the aqueous eluate by evaporation or distillation. Suitable evaporative means include reduced pressure evaporation, simple effect evaporation, multiple effect evaporation, or other evaporative means.

(III) Compositions Comprising the Specialty Formulations

Still another aspect of the present disclosure encompasses compositions comprising the specialty formulations comprising compounds of Formula (I), wherein the compositions have utility in a variety of applications. For example, compositions comprising the formulations disclosed herein may have nutritional uses (e.g., food/feed composition, dietary supplements, and the like), industrial uses (e.g., etching agents, electronic chemicals, polymers, thin film coatings, and so forth), or agricultural uses (e.g., agrochemical formulations, and the like). The compositions may be solid (e.g., powdered, granulated, pelleted, shaped, solid matrix, layered, encapsulated, and so forth) or liquid (which includes emulsions).

(a) Nutritional Compositions

In some embodiments, the compositions may have nutritional or dietary uses. Examples of suitable nutritional compositions include, without limit, food compositions, nutritional supplements, dietary supplements, feed compositions, feed premixes, pet foods, pet food supplements, feline urinary tract health food, and the like. Accordingly, the nutritional compositions comprise a specialty formulation comprising compounds of Formula (I) and at least one agent chosen from nutritional agents, bioactive agents, excipients, or combinations thereof.

(i) Nutritional Agents

Nutritional agents provide calories and include carbohydrate sources, protein sources, fat sources, or combinations thereof.

In some embodiments, the nutritional agent may comprise at least one carbohydrate source. The carbohydrate source may be of plant, microbial, or animal origin. Examples of suitable plant sources of carbohydrates include, without limit, grains such as wheat, oats, rice, rye, and so forth; legumes such as soy, peas, beans, and the like; corn; grasses; potatoes; vegetable plants; and plant fruits. The carbohydrate may be a monosaccharide such as pentose, glucose, galactose, and so forth; a disaccharide such as sucrose, lactose, maltose, and the like; an oligosaccharide such as a fructo-oligosaccharide, galactose-oligosaccharide, mannanoligosaccharide, etc.; or a polysaccharide such as starch, glycogen, cellulose, arabinoxylan, pectin, gum, chitins, and so forth.

In other embodiments, the nutritional agent may comprise at least one protein source. The protein source may be derived from a plant. Non-limiting examples of suitable plants that provide a good source of protein include amaranth, arrowroot, barley, buckwheat, canola, cassava, channa (garbanzo), legumes, lentils, lupin, maize, millet, oat, pea, potato, rice, rye, sorghum, soybean, sunflower, tapioca, triticale, wheat, seagrasses, and algae. Alternatively, the protein source maybe derived from an animal. For example, the animal protein source may be derived from a dairy product, bird eggs, or from the muscles, organs, connective tissues, or skeletons of land-based or aquatic animals.

In further embodiments, the nutritional agent may comprise at least one fat source. The fat source may be of plant, animal, or microbial origin. Non-limiting examples of plant derived fats include vegetable oils (e.g., canola oil, corn oil, cottonseed oil, palm oil, peanut oil, safflower oil, soybean oil, and sunflower oil) and oilseeds (e.g., canola seeds, cottonseeds, flax seeds, linseeds, Niger seeds, sesame seeds, soy beans, and sunflower seeds), distillers grains, or algae. Animal derived fats include, without limit, fish oils (e.g., menhaden oil, anchovy oil, albacore tuna oil, cod liver oil, herring oil, lake trout oil, mackerel oil, salmon oil, and sardine oil), high fat fish meal (e.g., menhaden meal, anchovy meal, herring meal, pollack meal, salmon meal, tuna meal, and whitefish meal), and animal fats (e.g., poultry fat, beef tallow, butter, pork lard, and whale blubber).

(ii) Bioactive Agents

Examples of suitable bioactive agents include vitamins, minerals, amino acids or amino acid analogs, antioxidants, organic acids, poly unsaturated fatty acids, essential oils, enzymes, prebiotics, probiotics, herbs, pigments, pharmaceutically active agents, or combinations thereof.

In some embodiments, the bioactive agents may be one or more vitamins. Suitable vitamins include vitamin A, vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), vitamin B12, vitamin C, vitamin D, vitamin E, vitamin K, other B-complex vitamins (e.g., choline, carnitine, adenine), or combinations thereof. The form of the vitamin may include salts of the vitamin, derivatives of the vitamin, compounds having the same or similar activity of a vitamin, and metabolites of a vitamin.

In other embodiments, the bioactive agent may be one or more minerals. Examples of suitable minerals include calcium, chromium, cobalt, copper, iodine, iron, magnesium, manganese, molybdenum, selenium, zinc, or combinations thereof. The mineral may be an inorganic mineral. Suitable inorganic minerals include, for example, metal sulfates, metal oxides, metal hydroxides, metal oxychlorides, metal carbonates, and metal halides. Alternatively, the mineral may be an organic mineral, e.g., a metal chelate comprising a metal ion and an organic ligand. The organic ligand may be an amino acid, an amino acid analog, a proteinate, or an organic acid.

In further embodiments, the bioactive agent may be one or more amino acids. Non-limiting suitable amino acids include standard amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), non-standard amino acids (e.g., L-DOPA, GABA, 2-aminobutyric acid, and the like), amino acid analogs, or combinations thereof. Amino acid analogs include α-hydroxy analogs, as well side chain protected analogs or N-derivatized amino acids.

In alternate embodiments, the bioactive agent may be one or more antioxidants. Suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline (ethoxyquin), ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

In still other embodiments, the bioactive agent may be one or more organic acids. The organic acid may be a carboxylic acid or a substituted carboxylic acid. The carboxylic acid may be a mono-, di-, or tri-carboxylic acid. In general, the carboxylic acid may contain from about one to about twenty-two carbon atoms. Suitable organic acids, by way of non-limiting example, include acetic acid, adipic acid, butanoic acid, benzoic acid, cinnamaldehyde, citric acid, formic acid, fumaric acid, glutaric acid, glycolic acid, lactic acid, malic acid, mandelic acid, propionic acid, sorbic acid, succinic acid, tartaric acid, or combinations thereof. Salts of organic acids comprising carboxylic acids are also suitable for certain embodiments. Representative suitable salts include the ammonium, magnesium, calcium, lithium, sodium, potassium, selenium, iron, copper, and zinc salts of organic acids.

In yet other embodiments, the bioactive agent may be one or more poly unsaturated fatty acids. Suitable poly unsaturated fatty acids (PUFAs) include long chain fatty acids with at least 18 carbon atoms and at least two carbon-carbon double bonds, generally in the cis-configuration. In specific embodiments, the PUFA may be an omega fatty acid. The PUFA may be an omega-3 fatty acid in which the first double bond occurs in the third carbon-carbon bond from the methyl end of the carbon chain (i.e., opposite the carboxyl acid group). Suitable examples of omega-3 fatty acids include all-cis 7,10,13-hexadecatrienoic acid; all-cis-9,12,15-octadecatrienoic acid (alpha-linolenic acid, ALA); all-cis-6,9,12,15,-octadecatetraenoic acid (stearidonic acid); all-cis-8,11,14,17-eicosatetraenoic acid (eicosatetraenoic acid); all-cis-5,8,11,14,17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; and all-cis-6,9,12,15,18,21-tetracosenoic acid (nisinic acid). In an alternative embodiment, the PUFA may be an omega-6 fatty acid in which the first double bond occurs in the sixth carbon-carbon bond from the methyl end of the carbon chain. Examples of omega-6 fatty acids include all-cis-9,12-octadecadienoic acid (linoleic acid); all-cis-6,9,12-octadecatrienoic acid (gamma-linolenic acid, GLA); all-cis-11,14-eicosadienoic acid (eicosadienoic acid); all-cis-8,11,14-eicosatrienoic acid (dihomo-gamma-linolenic acid, DGLA); all-cis-5,8,11,14-eicosatetraenoic acid (arachidonic acid, AA); all-cis-13,16-docosadienoic acid (docosadienoic acid); all-cis-7,10,13,16-docosatetraenoic acid (adrenic acid); and all-cis-4,7,10,13,16-docosapentaenoic acid (docosapentaenoic acid). In yet another alternative embodiment, the PUFA may be an omega-9 fatty acid in which the first double bond occurs in the ninth carbon-carbon bond from the methyl end of the carbon chain, or a conjugated fatty acid, in which at least one pair of double bonds are separated by only one single bond. Suitable examples of omega-9 fatty acids include cis-9-octadecenoic acid (oleic acid); cis-11-eicosenoic acid (eicosenoic acid); all-cis-5,8,11-eicosatrienoic acid (mead acid); cis-13-docosenoic acid (erucic acid), and cis-15-tetracosenoic acid (nervonic acid). Examples of conjugated fatty acids include 9Z,11E-octadeca-9,11-dienoic acid (rumenic acid); 10E,12Z-octadeca-9,11-dienoic acid; 8E,10E,12Z-octadecatrienoic acid (α-calendic acid); 8E,10E,12E-octadecatrienoic acid (β-Calendic acid); 8E,10Z,12E-octadecatrienoic acid (jacaric acid); 9E,11E,13Z-octadeca-9,11,13-trienoic acid (α-eleostearic acid); 9E,11E,13E-octadeca-9,11,13-trienoic acid (β-eleostearic acid); 9Z,11Z,13E-octadeca-9,11,13-trienoic acid (catalpic acid), and 9E,11Z,13E-octadeca-9,11,13-trienoic acid (punicic acid).

In additional embodiments, the bioactive agent may be one or more essential oils. Suitable essential oils include, but are not limited to, peppermint oil, cinnamon leaf oil, lemongrass oil, clove oil, castor oil, wintergreen oil, sweet orange, spearmint oil, cederwood oil, aldehyde C16, α terpineol, amyl cinnamic aldehyde, amyl salicylate, anisic aldehyde, benzyl alcohol, benzyl acetate, camphor, capsaicin, cinnamaldehyde, cinnamic alcohol, carvacrol, carveol, citral, citronellal, citronellol, p cymene, diethyl phthalate, dimethyl salicylate, dipropylene glycol, eucalyptol (cineole), eugenol, iso-eugenol, galaxolide, geraniol, guaiacol, ionone, listea cubea, menthol, menthyl salicylate, methyl anthranilate, methyl ionone, methyl salicylate, a phellandrene, pennyroyal oil, perillaldehyde, 1 or 2 phenyl ethyl alcohol, 1 or 2 phenyl ethyl propionate, piperonal, piperonyl acetate, piperonyl alcohol, D pulegone, terpinen 4 ol, terpinyl acetate, 4 tert butylcyclohexyl acetate, thyme oil, thymol, metabolites of trans-anethole, vanillin, ethyl vanillin, derivatives thereof, or combinations thereof.

In still other embodiments, the bioactive agents may be one or more probiotics or prebiotics. Probiotics and prebiotics include agents derived from yeast or bacteria that promote good digestive health. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.* Probiotics and prebiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pseudolongum.*

In alternate embodiments, the bioactive agent may be one or more enzymes or enzyme variants. Suitable non-limiting examples of enzymes include amylases, carbohydrases, cellulases, esterases, galactonases, galactosidases, glucanases, hemicellulases, hydrolases, lipases, oxidoreductases, pectinases, peptidases, phosphatases, phospholipases, phytases, proteases, transferases, xylanases, or combinations thereof.

In further embodiments, the bioactive agent may be one or more herbals. Suitable herbals and herbal derivatives, as used herein, refer to herbal extracts, and substances derived from plants and plant parts, such as leaves, flowers and roots, without limitation. Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, scullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca, or combinations thereof.

In still other embodiments, the bioactive agent may be one or more natural pigments. Suitable pigments include, without limit, actinioerythrin, alizarin, alloxanthin, β-apo-2'-carotenal, apo-2-lycopenal, apo-6'-lycopenal, astacein, astaxanthin, azafrinaldehyde, aacterioruberin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-α-carotenone, semi-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene, or combinations thereof.

In yet other embodiments, the bioactive agent may be one or more pharmaceutically acceptable agents. Non-limiting examples of pharmaceutically acceptable agents include an acid/alkaline-labile drug, a pH dependent drug, or a drug that is a weak acid or a weak base. Examples of acid-labile drugs include statins (e.g., pravastatin, fluvastatin and atorvastatin), antibiotics (e.g., penicillin G, ampicillin, streptomycin, erythromycin, clarithromycin and azithromycin), nucleoside analogs [e.g., dideoxyinosine (ddI or didanosine), dideoxyadenosine (ddA), dideoxycytosine (ddC)], salicylates (e.g, aspirin), digoxin, bupropion, pancreatin, midazolam, and methadone. Drugs that are only soluble at acid pH include nifedipine, emonapride, nicardipine, amosulalol, noscapine, propafenone, quinine, dipyridamole, josamycin, dilevalol, labetalol, enisoprost, and metronidazole. Drugs that are weak acids include phenobarbital, phenytoin, zidovudine (AZT), salicylates (e.g., aspirin), propionic acid compounds (e.g., ibuprofen), indole derivatives (e.g., indomethacin), fenamate compounds (e.g., meclofenamic acid), pyrroleakanoic acid compounds (e.g., tolmetin), cephalosporins (e.g., cephalothin, cephalaxin, cefazolin, cephradine, cephapirin, cefamandole, and cefoxitin), 6-fluoroquinolones, and prostaglandins. Drugs that are weak bases include adrenergic agents (e.g., ephedrine, desoxyephedrine, phenylephrine, epinephrine, salbutamol, and terbutaline), cholinergic agents (e.g., physostigmine and neostigmine), antispasmodic agents (e.g., atropine, methantheline, and papaverine), curariform agents (e.g., chlorisondamine), tranquilizers and muscle relaxants (e.g., fluphenazine, thioridazine, trifluoperazine, chlorpromazine, and triflupromazine), antidepressants (e.g., amitriptyline and nortriptyline), antihistamines (e.g., diphenhydramine, chlorpheniramine, dimenhydrinate, tripelennamine, perphenazine, chlorprophenazine, and chlorprophenpyridamine), cardioactive agents (e.g., verapamil, diltiazem, gallapomil, cinnarizine, propranolol, metoprolol and nadolol), antimalarials (e.g., chloroquine), analgesics (e.g., propoxyphene and meperidine), antifungal agents (e.g., ketoconazole and itraconazole), antimicrobial agents (e.g., cefpodoxime, proxetil, and enoxacin), caffeine, theophylline, and morphine. In another embodiment, the drug may be a biphosphonate or another drug used to treat osteoporosis. Non-limiting examples of a biphosphonate include alendronate, ibandronate, risedronate, zoledronate, pamidronate, neridronate, olpadronate, etidronate, clodronate, and tiludronate. Other suitable drugs include estrogen, selective estrogen receptor modulators (SERMs), and parathyroid hormone (PTH) drugs. In yet another embodiment, the drug may be an antibacterial agent. Suitable antibiotics include aminoglycosides (e.g., amikacin, gentamicin, kanamycin, neomycin, netilmicin, streptomycin, and tobramycin), carbecephems (e.g., loracarbef) a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprim-sulfamethoxazole), and tetracyclines (e.g., demeclocycline, doxycycline, minocycline, and oxytetracycline). In an alternate embodiment, the drug may be an antiviral protease inhibitor (e.g., amprenavir, fosamprenavir, indinavir, lopinavir/ritonavir, ritonavir, saquinavir, and nelfinavir). In a still another embodiment, the drug may be a cardiovascular drug. Examples of suitable cardiovascular agents include cardiotonic agents (e.g., digitalis (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallopamil, and diltiazem), and anticlot agents (e.g., dipyrimadole).

(iii) Excipients

A variety of excipients may be included in the nutritional compositions. Suitable excipients include fillers, binders, pH regulating agents, disintegrants, dispersing agents, preservatives, lubricants, coloring agents, flavoring agents, taste masking agents, or combinations thereof. In general, the excipient is a grade suitable for use in a nutritional composition.

In some embodiments, the excipient may comprise at least one filler. Non-limiting examples of suitable fillers (also called diluents) include cellulose, microcrystalline cellulose, cellulose ethers (e.g., ethyl cellulose, methyl cellulose, hydroxypropyl cellulose, hydroxypropyl methylcellulose, sodium carboxymethylcellulose, etc.), cellulose esters (i.e., cellulose acetate, cellulose butyrate, and mixtures thereof), starches (e.g., corn starch, rice starch, potato starch, tapioca starch, and the like), modified starches, pregelatinized starches, phosphated starches, starch-lactose, starch-calcium carbonate, sodium starch glycolate, glucose, fructose, sucrose, lactose, xylose, lactitol, mannitol, malitol, sorbitol, xylitol, maltodextrin, trehalose, calcium carbonate, calcium sulfate, calcium phosphate, calcium silicate, magnesium carbonate, magnesium oxide, talc, or combinations thereof. In other embodiments, the filler may comprise a polymer as specified below in section (III)(b).

In other embodiments, the excipient may comprise at least one binder. Examples of suitable binders include, without limit, starches (e.g., corn starch, potato starch, wheat starch, rice starch, and the like), pregelatinized starch, hydrolyzed starch, cellulose, microcrystalline cellulose, cellulose derivatives (e.g., methylcellulose, ethylcellulose, hydroxypropylcellulose, hydroxypropylmethylcellulose, sodium carboxymethylcellulose, and the like), saccharides (e.g., sucrose, lactose, and so forth), sugar alcohols (e.g., maltitol, sorbitol, xylitol, polyethylene glycol, and the like), alginates (e.g., alginic acid, alginate, sodium alginate, and so forth), gums (e.g., gum arabic, guar gum, gellan gum, xanthan gum, and the like), pectins, gelatin, C12-C18 fatty acid alcohols, polyvinylpyrrolidinone (also called copovidone), polyethylene oxide, polyethylene glycol, polyvinyl alcohols, waxes (e.g., candelilla wax, carnauba wax, beeswax, and so forth), or combinations of any of the foregoing.

In still other embodiments, the excipient may be a pH regulating agent. By way of non-limiting example, pH regulating agents include organic carboxylic acids (e.g., acetic acid, ascorbic acid, citric acid, formic acid, glycolic acid, gluconic acid, lactic acid, malic acid, maleic acid, propionic acid, succinic acid, tartaric acid, etc.) or salts thereof other acids (e.g., hydrochloric acid, boric acid, nitric acid, phosphoric acid, sulfuric acid, etc.), alkali metal or ammonium carbonates, bicarbonates, hydroxides, phosphates, nitrates, and silicates; and organic bases (such as, for example, pyridine, triethylamine (i.e., monoethanol amine), diisopropylethylamine, N methylmorpholine, N,N dimethylaminopyridine).

In additional embodiments, the excipient may be a disintegrant. Examples of suitable disintegrants include, without limit, povidone, crospovidone, croscarmellose sodium, sodium carboxymethylcellulose, carboxymethylcellose calcium, sodium starch glycolate, cellulose, microcrystalline cellulose, methylcellulose, silicon dioxide (also called colloidal silicone dioxide), alginates (e.g., alginic acid, alginate, sodium alginate, and so forth), clays (e.g., bentonite), or combinations thereof.

In alternate embodiments, the excipient may be a dispersing agent. Suitable dispersing agents include, but are not limited to, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In yet additional embodiments, the excipient may be a preservative. Non limiting examples of suitable preservatives include antioxidants (such as, e.g., alpha-tocopherol, ascorbyl palmitate, butylated hydroxyanisole, butylated hydroxytoluene, citric acid, dihydroguaretic acid, potassium ascorbate, potassium sorbate, propylgallate, sodium bisulfate, sodium isoascorbate, sodium metabisulfate, sorbic acid, 4-chloro-2,6-ditertiarybutylphenol, and so forth), antimicrobials (such as, e.g., benzyl alcohol, cetylpryidine chloride, glycerine, parabens, propylene glycol, potassium sorbate, sodium benzoate, sorbic acid, sodium propionate, and the like), or combinations thereof.

In still other embodiments, the excipient may be a lubricant. Examples of suitable lubricants include metal stearate such as magnesium stearate, calcium stearate, zinc stearate, a polyethylene glycol, a poloxamer, colloidal silicon dioxide, glyceryl behenate, light mineral oil, hydrogenated vegetable oils, magnesium lauryl sulfate, magnesium trisilicate, polyoxyethylene monostearate, sodium stearoyl fumarate, sodium stearyl fumarate, sodium benzoate, sodium lauryl sulfate, stearic acid, sterotex, talc, or combinations thereof.

In yet other embodiments, the excipient may be a color additive. Suitable color additives include, but are not limited to, food, drug and cosmetic colors (FD&C), drug and cosmetic colors (D&C), or external drug and cosmetic colors (Ext. D&C). drug and cosmetic colors (D&C), or external drug and cosmetic colors (Ext. D&C). These colors or dyes, along with their corresponding lakes, and certain natural and derived colorants may be suitable for use in the compositions.

In alternate embodiments, the excipient may be a flavoring agent. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot). In still another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. In still another embodiment, the excipient may include a taste-masking agent.

In some embodiments, the excipient may be a taste masking agent. Suitable taste masking agents include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; or combinations thereof.

(b) Industrial Compositions

In other embodiments, compositions comprising the formulations disclosed herein may have industrial uses. For example, the compositions may be used as etching agents or electronic process chemicals in the semiconductor, energy, or electronic industries. In other embodiments, the compositions may be used as polymers or copolymers in the manufacture of plastics used in beverage containers, food containers, food packaging products, food service ware, consumer product packaging, and the like. In still other embodiments, the compositions may be used as polymer/copolymer thin films in specialty coating applications, e.g., coating medical devices or quantum dots coatings. In alternate embodiments, the compositions may be used as wetting agents, demulsifiers, or processing aids in metal processing, textile processing, wood and paper processing, oil harvesting, and/or oil processing and reclamation processes.

Accordingly, the compositions detailed herein comprise a specialty formulation comprising compounds of Formula (I) and one or more agents chosen from solvents, surfactants, wetting agents, polymers, plasticizers, binders, fillers, thickening agents, foam control agents, dispersants, disintegrants, pH regulating agents, chelating agents, preservatives, pigments, heat stabilizers, UV/light stabilizers, flame retardants, biocides, processing aids, thermal modifiers, impact modifiers, blowing agents, lubricants, nucleating agents, or combinations thereof.

(i) Agents

In some embodiments, the agent may be a solvent. The solvent may be organic or inorganic. Suitable organic solvents include, without limit, oxygenated solvents (such as alcohols, esters, ketones, glycol ethers, glycol ether esters, hydroxyethers, and alkoxy propanols), hydrocarbon solvents (such as aliphatic and aromatic hydrocarbons), and halogenated solvents (such as chlorinated hydrocarbons). Suitable inorganic solvents include water and ammonia.

In further embodiments, the agent may a surfactant. The surfactant may be a nonionic surfactant, an anionic surfactant, or a cationic surfactant. Non-limiting examples of suitable nonionic surfactants (including zwitterionic surfactants that have no net charge) include alcohol ethoxylates, alkyl phenol ethoxylates (e.g., nonylphenyl ethoxylate), thiol ethoxylates, fatty acid ethoxylates, glycerol esters, hexitol esters, amine ethoxylates, alkylamide ethoxylates, and imide ethoxylates. Suitable anionic surfactants include, but are not limited to, alkyl sulfates, alkyl ether sulfates, sulfated alkanolamides, glyceride sulfates, dodecyl benzene sulfonates, alkylbenzene sulfonates, alpha olefin sulfonates, and sulfocarboxylic compounds. Non-limiting examples of suitable cationic surfactants include alkyl amines, quaternary alkyl ammoniums, ester amines, and ether amines.

In still other embodiments, the agent may be a wetting agent. Suitable wetting agents include but are not limited to nonionic surfactants such as polyoxyethylene surfactants, block co-polymer surfactants, alkyl polyglucoside surfactants, modified methyl capped block co-polymer surfactants, multibranched co-polymer surfactants, anionic surfactants, and cationic surfactants.

In alternate embodiments, the agent may be a polymer. Examples of suitable polymers include, without limitation, polymers of acrylates, acrylic acids, acrylonitriles, aminoacrylates, alkylene succinates, alkylene oxalates, amides, amines, anhydrides, arylates, carbonates, cellulose, cellulose derivatives, caprolactone, cyanoacrylates, dihydropyrans, dioxanes, dioxanones, ether ether ketones, ethylene glycol, ethylene oxide, fumarates, hydroxyalkanoates, hydroxylesters, imides, ketals, lactides, methacrylates, methyl olefins, orthoesters, phosphazines, pyridine, pyridine derivatives, styrenes, styrene derivatives, terephthalates, trimethylene carbonate, urethanes, vinyl acetates, vinyl esters, vinyl ketones, vinyl halides, derivatives, isomers, mixtures thereof, or co-polymers thereof.

In other embodiments, the agent may be a plasticizer. Examples of suitable plasticizers include but are not limited to adipates, sebecates/azelates, benzoates/dibenzoates, citrates, cyclohexanoates, epoxy esters, phosphate esters, polaxamers, polyethylene glycols, orthophthalates, terephthalates, trimellitates, or combinations thereof.

In further embodiments, the agent may a binder (i.e., film former). Non-limiting examples of suitable binders include acrylic resins, latex (i.e., vinyl-acrylic or PVA) resins, vinyl acetate/ethylene (VAE) resins, polyester resins, phenolic resins, alkyd resins, urethanes resins, melamine resins, and epoxy resins.

In still other embodiments, the agent may be a filler. Non-limiting examples of suitable fillers include cellulose, methylcellulose, carboxymethylcellulose, microcrystalline cellulose, calcium sulfate, calcium carbonate, magnesium carbonate, dibasic calcium phosphate, magnesium carbonate, magnesium oxide, calcium silicate, sodium chloride, titanium dioxide, talc, glass, mica, calcinated clay, red mud, dolomite, modified starches, lactose, sucrose, mannitol, sorbitol, or combinations thereof.

In alternate embodiments, the agent may be a thickening agent (i.e., rheological additive). Suitable thickening agents include without limit cellulosic ethers (such as hydroxycellulose, hydroxypropyl cellulose, hydroxymethylpropyl cellulose, hydroxyethyl cellulose, carboxymethyl cellulose, methylhydroxyethyl cellulose), polyvinylpyrrolidone, poly(vinylpyridine-N-oxide), acrylics, vinyl acrylics, bentonites, starches, gums, and combinations thereof.

In further embodiments, the agent may be a foam control agent (i.e., defoamer). Non-limiting examples of suitable foam control agents include defoamers based on ethylene oxide/propylene oxide copolymers, defoamers based on polymers with silicon backbones (e.g., silicone oils, polysiloxane, etc.), oil based defoamers (e.g., mineral oil, vegetable oil, long chain fatty acids, or fatty acid esters), or powder defoamers (e.g., silica).

In additional embodiments, the agent may be a dispersant. Suitable dispersants include without limit phosphonates, carboxymethyl inulin, sodium hexametaphosphate, sodium tripolyphosphate, tetrasodium pyrophosphate, potassium tripolyphosphate, and acrylic polymers.

In yet further embodiments, the agent may be a disintegrant. Suitable disintegrants include without limit starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth.

In alternate embodiments, the agent may be a pH regulating agent. Non-limiting examples of suitable pH regulating agents include organic carboxylic acids (e.g., acetic acid, ascorbic acid, citric acid, formic acid, glycolic acid, gluconic acid, lactic acid, malic acid, maleic acid, propionic acid, succinic acid, tartaric acid, etc.) or salts thereof other acids (e.g., hydrochloric acid, boric acid, nitric acid, phosphoric acid, sulfuric acid, etc.), alkali metal or ammonium carbonates, bicarbonates, hydroxides, phosphates, nitrates, and silicates; and organic bases (such as, for example, pyridine, triethylamine (i.e., monoethanol amine), diisopropylethylamine, N methylmorpholine, N,N dimethylaminopyridine.

In other embodiments, the agent may be a chelating agent. Suitable chelating agents include but are not limited to EDTA, DTPA, HEDP, HEDTA, NTA, HEIDA, PBTC, phosphonates, carboxymethyl inulin, trisodium phosphate, sodium hexametaphosphate, sodium tripolyphosphate, tetrasodium pyrophosphate, potassium tripolyphosphate, tetrapotassium pyrophosphate, citric acid, gluconic acid, sodium gluconate, and DTPMP.

In further embodiments, the agent may be a preservative. Non-limiting examples of suitable preservatives include antioxidants, such as alpha-tocopherol or ascorbate, and antimicrobials, such as parabens, chlorobutanol, phenol, glutaraldehyde, benzoic acid, quaternary ammonium salts, bronopol, hydrogen peroxide, sodium dichloroisocyanurate, and sodium hypochlorite.

In still other embodiments, the agent may be a pigment (or coloring agent). Pigments are finely ground particles or powders that provide coloring and hiding to paint formulations. The pigments may be prime pigments, which provide whiteness or color and hiding, or extender pigments, which ensure proper spacing of the prime pigments to avoid crowding and loss of hiding. In some embodiments, the prime pigment may be titanium dioxide or zinc oxide, the predominant white pigments. The prime pigments may also include organic or inorganic color pigments (or color agents). Color pigments or color agents are well-known in the art. Non-limiting examples color pigments include zinc yellow, benzidine yellow, chrome oxide green, phthalocyanine green, phthalocyanine blues, vermilion, pigment brown 6, red 170, dioxazine violet, carbon black, and iron(II) oxide. Suitable extender pigments (or extenders) include, without limit, clay (e.g., kaoline clay), silica, silicates, diatomaceous silica, quartz sand, calcium carbonate (also called limestone), barite, talc, and zinc oxide. Suitable coloring agents include, but are not limited to, food, drug and cosmetic colors (FD&C), drug and cosmetic colors (D&C), external drug and cosmetic colors (Ext. D&C), and other dyes known in the industry.

In some embodiments, the agent may be a heat stabilizer. Heat stabilizers generally comprise metal compounds such as metal soaps, metal salts, and organometallic compounds. The major metals contained in heat stabilizers include calcium, tin, zinc, barium, and lead. Non-limiting examples of suitable heat stabilizers include calcium-zinc stabilizer, calcium-organic stabilizer, (e.g., calcium acetylacetonate, zinc acetylacetonate), calcium stearate, zinc stearate, methyl tin stabilizer, organotin mercaptides, and combinations thereof.

In other embodiments, the agent may be a UV stabilizer or light stabilizer. Suitable UV stabilizers or light stabilizers include, without limit, 2-(2'-hydroxy-5'-methylphenyl)-benzotriazole, 2-hydroxy-4-octoxy benzophenone, 2-(2'-hydroxy-5'-tert-octylphenyl) benzotriazole, 2-(2'-hydroxy-3, 5'-ditert-butylphenyl)-benzotriazole, 2-(2'-hydroxy-3,5'-ditert-butylphenyl)-5-chloro benzotriazole, 2-(2'-hydroxy-3'-tert-butyl-5'-methylphenyl)-5-chloro benzotriazole, 2-hydroxy-4-methoxy benzophenone, poly[1-(2'-hydroxyethyl)-2,2,6,6-tetramethyl-4-hydroxy piperidylsuccinate, bis (2,2,6,6,-tetramethyl-4-piperidine) sebacate, 2-hydroxy-4-methoxy benzophenone-5-sulfonic acid, 2-phenyl-1H-benzo[d]imidazole-5-sulfonic acid, 2-(2'-hydroxy-3'-5'-ditert-butyl) benzotriazole, 2,2'-dihydroxy-4-methoxy benzotriazole, hindered amine light stabilizers (HALS), titanium dioxide and combinations thereof.

In still other embodiments, the agent may be a fire retardant or smoke suppressor. Non-limiting examples of suitable fire retardants/smoke suppressants include alumina trihydrate, magnesium hydroxide, antimony trioxide, hydromagnesite, copper clays, molybdates, borates, chlorendic acid derivatives, chlorinated paraffins, decabromodiphenyl ether, decabromodiphenyl ethane, brominated polystyrenes, brominated epoxy oligomers, tetrabromophthalic anhydride, tetrabisphenol A, hexabromocyclododecane, triphenyl phosphate, resorcinol bis(diphenylphosphate, bisphenol A diphenyl phosphate, tricresyl phosphate, dimethyl methylphosphonate, alumina diethyl phosphinate, tris(2,3-dibromopropyl phosphate, tris(1,3-dichloro-2-propyl)phosphate, (2-chlorethyl)dichloroisopentyldiphosphate, and combinations thereof.

In other embodiments, the agent may be a biocide. Non-limiting examples of suitable biocide include copper 2-ethylhexanoate, zinc pyrithione, 10,10'-oxybisphenooxyarsine, diodomethyl-p-tolylsulfone, 3-iodo-2-propynyl butylcarbamate, N-(trichloromethylthio)phthalimide, n-octyl-, dichloro n-ocyl-isothiazolinone, butylbenzisothiazolinone, and combinations thereof.

In yet other embodiments, the agent may be a processing aid. Processing aids include, but are not limited to, acrylic processing aids, acrylate copolymers, styrene-acrylonitrile copolymers, methylmethacylate-styrene-vinylacetate copolymers, and combinations thereof.

In further embodiments, the agent may be a thermal modifier. Non-limiting examples of suitable thermal modifiers include methyacrylate-butadiene-styrene terpolymers (e.g., Clearstrength E-920), acrylonitrile-butadiene-styrene copolymers, alpha-methylstyrene copolymers, ethylene-propylene copolymers, ethylene copolymers, acrylate modifiers (e.g., phenoxyethyl methacrylate, ethylene glycol dimethacrylate, dimethacrylate, 1,3-butylene glycol, hexanediol dimethacrylate, trimethyacrylate ester, trimethyacrylate, trimethylolpropane), and combinations thereof.

In still other embodiments, the agent may be an impact modifier. Impact modifiers include without limit ethylene copolymers, ethylene/butyl acrylate/glycidyl methacrylate copolymers, ethylene-propylene copolymers, acrylic impact modifiers, acrylonitrile-butadiene-styrene copolymers, acrylonitrile-styrene-acrylate copolymers, styrene-butadiene-styrene copolymers, styrene-ethylene-butadiene-styrene copolymers, chlorinated polyethylene, crosslinked polyacrylate, and combinations thereof.

In alternate embodiments, the agent may be a blowing agent. Non-limiting examples of suitable blowing agents include azodicarbonamide or other azo-based compounds, hydrazine nitrate or other hydrazine-based compounds, endothermic chemical foaming agents (CFAs), exothermic CFAs, endothermic/exothermic CFA blends, hydrocarbons (e.g., pentane, isopentane, cyclopentane), isocyanate, and combinations thereof.

In other embodiments, the agent may be a lubricant or co-stabilizer. Suitable lubricants or co-stabilizers include without limit polyols, epoxidized esters, epoxidized oils, polyethylene waxes, oxidized polyethylene waxes, paraffins, metallic soaps (e.g., calcium stearate, zinc stearate, etc.), esters (e.g., polyethylene mono/di/tri stearate, glycerol monostearate, glyceryl monooleate, Montan wax, stearyl stearate, distearyl phthalate), amides (e.g., erucamide, oleamido, stearamide, ethylene bis(stearamide), and so forth), fatty acids (e.g., lauric acid, stearic acid, oleic acid, etc.), fatty alcohols (e.g., cetyl alcohol, stearyl alcohol, behenoyl alcohol, and so forth), and combinations thereof.

In still other embodiments, the agent may be a nucleating agent. Non-limiting examples of suitable nucleating agents include N,N'-ethylene-bis-stearamide (EBS), LAK-301 (an aromatic sulfonate derivative), talc, sodium benzoate, calcium carbonate, calcium salts of suberic acid, calcium salts of pimelilc acid, beta-cyclodextrin, polyoxymethylene, magnesium, sodium, or zinc phenylphosphonate, cyanuric acid, uracil, thymine, nitroimidazole, fatty acid amides, and combinations thereof.

(c) Agricultural Compositions

In yet other embodiments, the composition may have uses in agricultural, forestry, or landscaping. For example, the compositions may be used as agrochemical formulations, emulsifiable agricultural concentrates, and so forth. Said compositions comprise a specialty formulation comprising compounds of Formula (I) and at least one agent chosen from herbicides, fungicides, insecticides, fertilizers, solvents, surfactants, binders, fillers, wetting agents, thickening agents, foam control agents, dispersants, disintegrants, pH regulating agents, chelating agents, preservatives, pigments, or combinations thereof.

(i) Agents

In some embodiments, the agent may be one or more herbicides. Non-limiting examples of suitable herbicides include imidazolinone, acetochlor, acifluorfen, aclonifen, acrolein, AKH-7088, alachlor, alloxydim, ametryn, amidosulfuron, amitrole, ammonium sulfamate, anilofos, asulam, atrazine, azafenidin, azimsulfuron, BAS 620H, BAS 654 00H, BAY FOE 5043, benazolin, benfluralin, benfuresate, bensulfuron-methyl, bensulide, bentazone, benzofenap, bifenox, bilanafos, bispyribac-sodium, bromacil, bromobutide, bromofenoxim, bromoxynil, butachlor, butamifos, butralin, butroxydim, butylate, cafenstrole, carbetamide, carfentrazone-ethyl, chlormethoxyfen, chloramben, chlorbromuron, chloridazon, chlorimuron-ethyl, chloroacetic acid, chlorotoluron, chlorpropham, chlorsulfuron, chlorthal-dimethyl, chlorthiamid, cinmethylin, cinosulfuron, clethodim, clodinafop-propargyl, clomazone, clomeprop, clopyralid, cloransulam-methyl, cyanazine, cycloate, cyclosulfamuron, cycloxydim, cyhalofop-butyl, 2,4-D, daimuron, dalapon, dazomet, 2,4DB, desmedipham, desmetryn, dicamba, dichlobenil, dichlorprop, dichlorprop-P, diclofop-methyl, difenzoquat metilsulfate, diflufenican, dimefuron, dimepiperate, dimethachlor, dimethametryn, dimethenamid, dimethipin, dimethylarsinic acid, dinitramine, dinocap, dinoterb, diphenamid, diquat dibromide, dithiopyr, diuron, DNOC, EPTC, esprocarb, ethalfluralin, ethametsulfuron-methyl, ethofumesate, ethoxysulfuron, etobenzanid, fenoxaprop-P-ethyl, fenuron, ferrous sulfate, flamprop-M, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, flupropanate, flupyrsulfuron-methyl-sodium, flurenol, fluridone, flurochloridone, fluroxypyr, flurtamone, fluthiacet-methyl, fomesafen, fosamine, glufosinate-ammonium, glyphosate, glyphosinate, halosulfuron-methyl, haloxyfop, HC-252, hexazinone, imazamethabenz-methyl, imazamox, imazapyr, imazaquin, imazethapyr, imazosulfuron, imidazilinone, indanofan, ioxynil, isoproturon, isouron, isoxaben, isoxaflutole, lactofen, lenacil, linuron, MCPA, MCPA-thioethyl, MCPB, mecoprop, mecoprop-P, mefenacet, metamitron, metazachlor, methabenzthiazuron, methylarsonic acid, methyldymron, methyl isothiocyanate, metobenzuron, metobromuron, metolachlor, metosulam, metoxuron, metribuzin, metsulfuron-methyl, molinate, monolinuron, naproanilide, napropamide, naptalam, neburon, nicosulfuron, nonanoic acid, norflurazon, oleic acid (fatty acids), orbencarb, oryzalin, oxadiargyl, oxadiazon, oxasulfuron, oxyfluorfen, paraquat dichloride, pebulate, pendimethalin, pentachlorophenol, pentanochlor, pentoxazone, petroleum oils, phenmedipham, picloram, piperophos, pretilachlor, primisulfuron-methyl, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, pyrithiobac-sodium, quinclorac, quinmerac, quinoclamine, quizalofop, quizalofop-P, rimsulfuron, sethoxydim, siduron, simazine, simetryn, sodium chlorate, STS system (sulfonylurea), sulcotrione, sulfentrazone, sulfometuron-methyl, sulfosulfuron, sulfuric acid, tar oils, 2,3,6-TBA, TCA-sodium, tebutam, tebuthiuron, terbacil, terbumeton, terbuthylazine, terbutryn, thenylchlor, thiazopyr, thifensulfuron-methyl, thiobencarb, tiocarbazil, tralkoxydim, tri-allate, triasulfuron, triaziflam, tribenuron-methyl, triclopyr, trietazine, trifluralin, triflusulfuron-methyl, vernolate, or combinations thereof.

In still other embodiments, the agent may be one or more fungicides. Suitable fungicides include, without limit, carbamate fungicides such as 3,3'-ethylenebis(tetrahydro-4,6-dimethyl-2H-1,3,5-thiadiazine-2-thione), zinc or manganese ethylenebis(dithiocarbamate), bis(dimethyldithiocarbamoyl)disulfide, zinc propylenebis(dithiocarbamate, bis(dimethyldithiocarbamoyl)ethylenediamine, nickel dimethyldithiocarbamate, methyl 1-(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate, and 5-methyl-10-butoxycarbonylamino-10,11-dehydrodibenzo (b,f)azepine; pyridine fungicides such as zinc bis(1-hydroxy-2(1H)pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalimide fungicides such as N-(2,6-diethylphenyl) phthalimide and N-(2,6-diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate; pentachloronitrobenzene; 1,4-dichloro-2,5-dimethoxybenzene; 5-methyl-s-triazol(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1-2,4-thiadiazole; 2,4-dichloro-6-(O-chloroanilino)-1,3,5-triazine; 2,3-dicyano-1,4-dithioanthraquinone; copper 8-quinolinate, polyoxine; validamycin; cycloheximide; iron methanearsonate; diisopropyl-1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)-5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H, 1,3,4-triazol-1-yl)-2-butanone; methyl-D, L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinimide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolo[3,2,1-i,j]quinoline-2-one; 3'-isopropoxy-2-methylbenzanilide; 1-[2-(2,4-dichlorophenyl)-4-ethyl-1,3-dioxorane-2-ylmethyl]-1H, 1,2,4-triaz ol; 1,2- benzisothiazoline-3-one; basic copper chloride; basic copper sulfate; N'-dichlorofluoromethylthio-N,N-dimethyl-N-phenylsulfamide; ethyl-N-(3-dimethylaminopropyl)thiocarbamate hydrochloride; piomycin; S,S-6-methylquinoxaline-2,3-diyldithiocarbonate; complex of zinc and manneb; di-zinc bis(dimethyldithiocarbamate) ethylenebis (dithiocarbamate) and glyphosate; chlorothalonil-based fungicides, strobilurin-based fungicides such as azoxystrobin, pyraclostrobin, and trifloxystrobin; and triazole-based fungicide such as myclobutanil, propiconazole, tebuconazol, tetraconazole, or combinations thereof.

In yet further embodiments, the agent may be at least one insecticide. Non-limiting examples of suitable insecticides include phosphoric insecticides such as O,O-diethyl O-(2-isopropyl-4-methyl-6-pyrimidinyl)phosphorothioate, O,O-dimethyl S-2-[(ethylthio)ethyl]phosphorodithioate, O,O-dimethyl O-(3-methyl-4-nitrophenyl)thiophosphate, O,O-dimethyl S—(N-methylcarbamoylmethyl) phosphorodithioate, O,O-dimethyl S—(N-methyl-N-formylcarbamoylmethyl) phosphorodithioate, O,O-dimethyl S-2-[(ethylthio)ethyl] phosphorodithioate, O,O-diethyl S-2-[(ethylthio)ethyl] phosphorodithioate, O,O-dimethyl-1-hydroxy-2,2,2-trichloroethylphophonate, O,O-diethyl-O-(5-phenyl-3-isooxazolyl)phosphorothioate, O,O-dimethyl O-(2,5-dichloro-4-bromophenyl) phosphorothioate, O,O-dimethyl O-(3-methyl-4-methylmercaptophenyl)thiophosphate, O-ethyl O-p-cyanophenyl phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl) methyl] O,O-diethyl phosphorodithioate, 2-chloro-1-(2,4-dichlorophenyl)vinyl diethylphosphate, O,O-diethyl O-(3-oxo-2-phenyl-2H-pyridazine-6-yl) phosphorothioate, O,O-dimethyl S-(1-methyl-2-ethylsulfinyl)-ethyl phosphorothiolate, O,O-dimethyl S-phthalimidomethyl phosphorodithioate, O,O-diethyl S—(N-ethoxycarbonyl-N-methylcarbamoylmethyl)phosphorodithioate, O,O-dimethyl S-[2-methoxy-1,3,4-thiadiazol-5-(4H)-onyl-(4)-methyl] dithiophosphate, 2-methoxy-4H-1,3,2-benzooxaphosphorine 2-sulfide, O,O-diethyl O-(3,5,6-trichloro-2-pyridyl) phosphorothiate, O-ethyl O-2,4-dichlorophenyl thionobenzene phosphonate, 5-[4,6-diamino-s-triazine-2-yl-methyl] O,O-dimethyl phosphorodithioate, O-ethyl O-p-nitrophenyl phenyl phosphorothioate, O,S-dimethyl N-acetyl phosphoroamidothioate, 2-diethylamino-6-methylpyrimidine-4-yl-diethylphosphorothionate, 2-diethylamino-6-methylpyrimidine-4-yl-dimethylphosphorothionate, O,O-diethyl O—N-(methylsulfinyl) phenyl phosphorothioate, O-ethyl S-propyl O-2,4-dichlorophenyl phosphorodithioate and cis-3-(dimethoxyphosphinoxy)N-methyl-cis-crotone amide; carbamate insecticides such as 1-naphthyl N-methylcarbamate, S-methyl N-[methylcarbamoyloxy]thioacetoimidate, m-tolyl methylcarbamate, 3,4-xylyl methylcarbamate, 3,5-xylyl methylcarbamate, 2-sec-butylphenyl N-methylcarbamate, 2,3-dihydro-2,2-dimethyl-7-benzofuranylmethylcarbamate, 2-isopropoxyphenyl N-methylcarbamate, 1,3-bis (carbamoylthio)-2-(N,N-dimethylamino)propane hydrochloride and 2-diethylamino-6-methylpyrimidine-4-yl-dimethylcarbamate; and other insecticides such as N,N-dimethyl N'-(2-methyl-4-chlorophenyl)formamidine hydrochloride, nicotine sulfate, milbemycin, 6-methyl-2,3-quinoxalinedithiocyclic S,S-dithiocarbonate, 2,4-dinitro-6-sec-butylphenyl dimethylacrylate, 1,1-bis(p-chlorophenyl) 2,2,2-trichloroethanol, 2-(p-tert-butylphenoxy)isopropyl-2'-chloroethylsulfite, azoxybenzene, di-(p-chlorophenyl)-cyclopropyl carbinol, di[tri(2,2-dimethyl-2-phenylethyl)tin] oxide, 1-(4-chlorophenyl)-3-(2,6-difluorobenzoyl) urea, S-tricyclohexyltin O,O-diisopropylphosphorodithioate, or combinations thereof.

In still other embodiments, the agent may be a fertilizer. A variety of fertilizers are suitable for inclusion in the compositions. The fertilizer may be a single nutrient fertilizer (N, P, or K), a binary fertilizer (e.g., NP, NK, or PK), a NPK fertilizer, or a multinutrient fertilizer (e.g., may provide one or more of calcium, magnesium, sulfur, copper, iron, manganese, molybdenum, zinc, boron, silicon, cobalt, or vanadium). The fertilizer may be of natural origin or synthetic origin, and the fertilizer may be liquid or solid, and may provide slow or controlled release.

In alternate embodiments, the agent may be one or more solvents, surfactants, binders, fillers, wetting agents, thickening agents, foam control agents, dispersants, disintegrants, pH regulating agents, chelating agents, preservatives, or pigments, examples of which are detailed above in section (III)(b).

(IV) Processes for Preparing Derivatives of Compounds of Formula (I)

A further aspect of the present disclosure encompasses processes for preparing derivatives of the compounds of Formula (I) wherein the derivatives comprise low levels of sulfate ions and bisulfate salts.

(a) Metal Chelates or Metal Salts of Compounds of Formula (I)

Compounds of Formula (I) may be converted to metal chelates or metal salts by contacting the formulations disclosed above in section (I) with a source of metal ions. Suitable sources of metal ions include metal oxides, metal carbonates, or metal hydroxides. Generally, the metal ions are chosen from calcium ions, chromium ions, cobalt ions, copper ions, iron ions, manganese ions, silver ions, sodium ions, zinc ions, or combinations thereof. Where the metal ion is copper, manganese, chromium, cobalt and iron, it is preferably divalent. The ratio of compounds of Formula (I) to metal ion in the chelate molecule may generally vary from 1:1 to 3:1 or higher. Typically, a metal chelate may comprise a mixture of 1:1, 2:1 and 3:1 species. In specific embodiments, the average ratio of compounds of Formula (I) to metal ion in the chelate molecule may generally vary from 1.5:1 to 2.5:1.

Generally, the reaction is conducted substantially at atmospheric pressure, and the reaction mass is heated to a temperature in the 90° to 130° C. range. After the reaction is substantially complete, heating of the reaction mass is continued to produce a substantially dried product. Ultimately, the free water content is reduced to about 2% by weight or less, and the product mass transitions to free-flowing particulate solid.

The metal chelates or metal salts of compounds of Formula (I) prepared from the formulations detailed in section (I) have low levels of sulfate ions and bisulfate salts. For example, metal chelates or metal salts of compounds of Formula (I) comprise about 2700 ppm or less of sulfate ion and about 500 ppm or less of bisulfate salt.

(b) Cyclic Dimer Derivatives

In some embodiments, compounds of Formula (I) may be subjected to a cyclization reaction to form a cyclic dimer derivative. The process comprises contacting the formulation detailed above in section (I) with an acid catalyst under dehydration conditions to convert compounds of Formula (I) to the cyclic dimer compound of Formula (II):

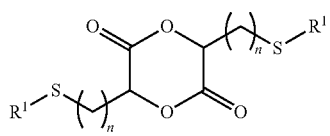

wherein $R^1$ and n are as defined above in section(I)(a).

(i) Acid Catalyst

A variety of acid catalysts may be used in the cyclization reaction. In some embodiments, the acid catalyst may be chosen from organic acids, inorganic acids, and solid resins. Exemplary acid catalysts include, without limitation, phosphoric acid, acetic acid, boric acid, hydrochloric acid, trifluoroacetic acid, methanesulfonic acid, ortho- meta- and para-toluenesulfonic acid, polyphosphoric acid, sulfuric acid, tosylic acid, xylenesulfonic acid, Dowex resins, Amberlyst resins, Zn dust, and Sn based catalysts (such as, for example, Sn dust, tin oxide, tin (II) chloride, dibutyltin dilaurate, and stannous octoate), germanium dioxide, antimony trioxide, zinc oxide, iron (III) oxide, aluminum oxide, silicon dioxide, titanium dioxide, mixtures and combinations thereof. In specific embodiments, the acid catalyst may be p-toluenesulfonic acid.

The acid catalyst may be added in a range of ratios to the compounds of Formula (I). In some aspects the amount of catalyst used in the reaction may range from 0.0001 mol % to about 5 mol % of the compounds of Formula (I). In some embodiments, the amount of acid catalyst used in the reaction may be less than about 5 mol %, less than about 2 mol %, or less than about 1 mol %. In other embodiments, the amount of acid catalyst used in the reaction may be about 0.001, 0.002, 0.003, 0.004, 0.005, 0.006, 0.007, 0.008, 0.009, or 0.010 mol % to the compounds of Formula (I).

(ii) Optional Solvent

The reaction may be performed in the presence of a solvent or the reaction may be performed neat. Where the reaction includes a solvent, the type of solvent may vary depending upon the identities of the reactants. Thus, the solvent may be a nonpolar solvent, a protic polar solvent, an aprotic polar solvent, or a combination thereof. Non-limiting examples of suitable nonpolar solvents include anisole, benzene, butyl acetate, tert-butyl methyl ether, chlorobenzene, chloroform, chloromethane, cyclohexane, dichloromethane, dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, xylene and combinations thereof. Examples of suitable protic polar solvents include without limit water, alcohols (e.g., methanol, ethanol, isopropanol, n-propanol, isobutanol, n-butanol, s-butanol, t-butanol), diols (e.g., propylene glycol and the like), organic acids (e.g., formic acid, acetic acid, and so forth), amides (e.g., formamide, acetamide, and the like), and combinations of any of the above. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, or combinations thereof. In exemplary embodiments, the solvent is chosen from toluene, xylene, anisole, or mixtures thereof.

The volume-to-mass ratio of the solvent to the compounds of Formula (I) can and will vary. Typically, the volume-to-mass ratio of the solvent to the compounds of Formula (I) may range from about 1:1 to about 100:1. In various embodiments, the volume-to-mass ratio of the solvent to the compound of Formula (I) may range from about 1:1 to about 3:1, from about 3:1 to about 10:1, from about 10:1 to about 30:1, or from about 30:1 to about 100:1. In some embodiments, the volume-to-mass ratio of the solvent to the compounds of Formula (I) may be about 30:1, or about 60:1.

(iii) Reaction Conditions

In general, the reaction is conducted under dehydration conditions to promote cyclization and formation of the cyclic dimer. In certain embodiments, dehydration may be accomplished via distillation. For example, the reaction may be subjected to simple distillation, fractional distillation, azeotropic distillation, steam distillation, vacuum distillation, distillation using a Dean Stark trap or another similar trap, azeotropic distillation using a Dean Stark or another similar trap, and the like. In other embodiments, dehydration may be accomplished via a drying reagent which may include molecular sieves, calcium sulfate, magnesium sulfate, sodium sulfate, potassium hydroxide, potassium carbonate, and the like.

The temperature at which the reaction takes place may vary in different embodiments and over the course of the reaction. In one embodiment, the reaction may be carried out at a temperature ranging from about 100° C. and about 200° C. In another embodiment, the reaction may be conducted at a temperature of about 100° C., 110° C., 120° C., 130° C., 140° C., 150° C., 160° C., 170° C., 180° C., 190° C., 200° C., or at a range between and including any two of these values. In another embodiment, the temperature may range from about 130° C. and about 150° C. In yet another embodiment, the temperature may range from about 110° C. and about 120° C. In general, the reaction is conducted at atmospheric pressure, but in certain embodiments, the reaction may also be conducted above or below atmospheric pressure.

The duration of the reaction can and will vary. In general, the reaction may be allowed to proceed from several hours to several days. Typically, however, the reaction is allowed to proceed for a sufficient period of time until the reaction is complete, as determined by means well known to those of skill in the art. In this context, the final reaction mixture contains a significantly diminished amount of the compounds of Formula (I) and a significantly increased amount of the compound of Formula (II) compared to the amounts of each present at the beginning of the reaction. In some embodiments, the reaction may be allowed to proceed for a period of time ranging from about 1 hour to about 10 hours. In another embodiment, the reaction may be allowed to proceed for a period of time ranging from about 1 hour to about 5 hours. In a preferred embodiment, the reaction may be allowed to proceed for a period for about 3 hours to about 5 hours.

The yield of the compound of Formula (II) can and will vary. In general, yield of the compound of Formula (II) will be at least about 15%, at least about 20%, 30%, at least about 40%, at least about 50%, at least about 60%, at least about 70%, at least about 80%, or at least about 90%.

The compound of Formula (II) may be isolated from the reaction mixture and/or purified by means including by size exclusion chromatography, high performance liquid chromatography (HPLC), ion-exchange chromatography, chiral chromatography, other types of chromatography, precipitation, distillation, or crystallization.

The compound of Formula (II) prepared from the formulation detailed above in section (I) has low levels of sulfate ions and bisulfate salts. For example, the compound of Formula (II) comprises about 2700 ppm or less of sulfate ion and about 500 ppm or less of bisulfate salt.

(iv) Applications

The cyclic dimer compounds of Formula (II) may be used in a variety of applications. Suitable applications include, without limit, use as plasticizers, emulsifiers, additives, processing aids, nutritive agents, antioxidant agents, antimicrobial agents, anticorrosive agents, and feed additives.

(c) Ester Derivatives

In other embodiments, the compounds of Formula (I) may undergo an esterification reaction to form ester derivatives. The process comprises contacting the formulation detailed above in section (I) with an alcohol, $R^3OH$, to convert the compounds of Formula (I) to ester compounds of Formula (III):

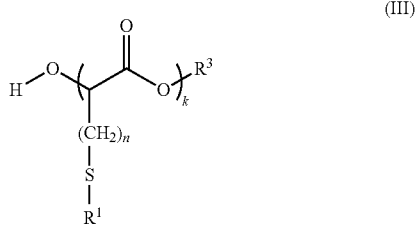

(III)

wherein $R^1$, n, and k are as defined above in section (I)(a), and $R^3$ is hydrocarbyl or substituted hydrocarbyl.

(i) Alcohol

In various embodiments, $R^3$ may be alkyl, substituted alkyl, alkenyl, substituted alkenyl, alkynyl, substituted alkynyl, aryl, or substituted aryl. The alkyl, alkenyl, and alkynyl may be linear, branched, or cyclic. In some embodiments, $R^3$ may be $C_1$ to $C_{30}$ alkyl, for example, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{24}$, $C_{26}$, $C_{28}$, or $C_{30}$ alkyl. In other embodiments, $R^3$ may be $C_1$ to $C_{30}$ alkenyl, for example, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{24}$, $C_{26}$, $C_{28}$, or $C_{30}$ alkenyl. In other embodiments, $R^3$ may be a substituted alkyl. For example the substituted alkyl may comprise one or more ether linkages, e.g., polyethers such as —$(CH(R')CH_2O)_mH$, or —$(CH(R')CH_2O)_mR''$, wherein R' is hydrogen, alkyl, substituted alkyl, hydroxy, or amino; R'' is alkyl, substituted alkyl, alkenyl, or substituted alkenyl; and m is an integer of 1 or greater. In some embodiments, the polyether may be poly(ethyleneoxide)alkyl.

In various embodiments, $R^3OH$ may be methanol, ethanol, 1-propanol, 2-propanol, 1-butanol, 2-butanol, 1-pentanol, 2-pentanol, 1-hexanol, 2-hexanol, 1-heptanol, 2-heptanol, 1-octanol, 2-octanol, 2-ethylhexanol, 3-ethylhexanol, 4-ethylhexanol, 1-methylheptanol, 2-methylheptanol, 3-ethylheptanol, 4-methylheptanol, 1-nonanol, 1-decanol, 1-undecanol, 1-dodecanol, 1-tridecanol, 1-tetradecanol, 1-pentadecanol, 1-hexadecanol, cis-9-hexadecen-1-ol, 1-n-heptadecanol, 1-octadecanol, 1-nonadecanol, 1-eicosanol, 1-heneicosaol, 1-docosanol, cis-13-docosen-1-ol, 1-tetracosanol, 1-hexacosanol, 1-octacosanol, 1-triacontanol, or an alcohol ethoxylate.

The amount of $R^3OH$ contacted with the compounds of Formula (I) can and will vary. In general, the mole-to-mole ratio of the compounds of Formula (I) to $R^3OH$ may range from about 1:0.1 to about 1:10. In various embodiments, the mole-to-mole ratio of the compounds of Formula (I) to $R^3OH$ may range from about 1:0.2 to about 1:8, from about 1:0.4 to about 1:6, from about 1:0.6 to about 1:5, from about 1:0.8 to about 1:4, from about 1:0.9 to about 1:3, or from about 1:1 to about 1:2.

(ii) Catalyst

In general, the reaction is conducted in the presence of a catalyst. The catalyst may be a chemical catalyst, such as a proton donor, an organometallic compound, such as tin compounds, or another chemical catalyst known in the art. Alternatively, the catalyst may be an enzyme catalyst, such as a lipase enzyme. Lipase enzymes can catalyze the formation (as well as hydrolysis) of ester linkages.

In embodiments in which the catalyst is a proton donor, a variety of proton donors may be used in the process. Non-limiting examples of suitable proton donor include acid salts (e.g., bisulfates, hydrosulfates), mineral acids (e.g., hydrogen halides such as hydrochloric acid, hydrobromic acid; halogen oxoacids such as hypochloric acid, chloric acid, perchloric acid, periodic acid; sulfuric acid; boric acid; nitric acid, phosphoric acid, etc.); sulfonic acids (e.g., methanesulfonic acid, p-toluenesulfonic acid); solid bound proton donors (e.g., Amberlyst 15, Amberlyst 35, and the like); ion exchange resins (e.g., Amberlite, Amberjet, Dowex, etc.); ionomers (e.g., polystyrene sulfonate, Nafion, Hycar and so forth); and ionic liquids having acidic characteristics.

The mole-to-mole ratio of the compounds of Formula (I) to the proton donor catalyst can and will vary depending upon the identity of the proton donor. In general, the mole-to-mole ratio of the compounds of Formula (I) to the proton donor may range from about 1:0.005 to about 1:0.25. In some embodiments, the mole-to-mole ratio of the compounds of Formula (I) to the proton donor may be about 1:0.01, about 1:0.02, about 1:0.04, about 1:0.05, about 1:0.06, about 1:0.08, about 1:0.10, about 1:0.12, about 1:0.14, about 1:0.16, about 1:0.18, or about 1:0.20.

(iii) Optional Solvent

The esterification reaction may be conducted in the absence of a solvent or in the presence of a solvent. In embodiments in which a solvent is present, the type of solvent may vary depending upon the reactants. Thus, the solvent may be a nonpolar solvent, a polar solvent, or a combination thereof. Non-limiting examples of suitable nonpolar solvents include benzene, butyl acetate, tert-butyl methyl ether, chlorobenzene, chloroform, chloromethane, cyclohexane, dichloromethane (DCM), dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Non-limiting examples of suitable polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In specific embodiments, the solvent may be toluene.

The volume-to-mass ratio of the solvent to the compounds of Formula (I) can and will vary. Typically, the volume-to-mass ratio of the solvent to the compounds of Formula (I) may range from about 1:1 to about 100:1. In various embodiments, the volume-to-mass ratio of the solvent to the compounds of Formula (I) may range from about 1:1 to about 3:1, from about 3:1 to about 10:1, from about 10:1 to about 30:1, or from about 30:1 to about 100:1.

(iv) Reaction Conditions

The reaction may be conducted at a temperature that ranges from about 30° C. to about 200° C. In certain embodiments, the temperature of the reaction may be about 40° C., 50° C., 60° C., 70° C., 80° C., 90° C., 100° C., 110° C., 120° C., 130° C., 140° C., or 150° C. In specific embodiments, the reaction may be conducted at a temperature from about 80° C. to about 150° C.

The duration of the reaction can and will vary. In general, the reaction may be allowed to proceed from about 1 hour to about 24 hours or more. In some embodiments, the reaction may be allowed to proceed overnight (or from about 12 to about 18 hours). Typically, however, the reaction is allowed to proceed for a sufficient period of time until the reaction has proceeded to the desired degree of completion, as determined by means well known to those of skill in the art. In embodiments in which the reaction is allowed to go to completion, a "completed reaction" generally means that the final reaction mixture contains a significantly diminished amount of the compounds of Formula (I) and a significantly increased amount of the ester compounds of Formula (III) compared to the amounts of each present at the beginning of the reaction.

The compounds of Formula (III) may be isolated from the reaction mixture by means known in the art. Suitable means include extracting, washing, precipitating, filtering, distilling, evaporating, drying, chromatography, and combinations thereof. Compounds of Formula (III) may comprise monomers, dimers, trimers, and/or longer oligomers. In some embodiments, individual monomers, dimers, etc. may be isolated.

The yield of the compounds of Formula (III) can and will vary. In general, yield of the compounds will be at least about 20%, at least about 30%, at least about 40%, at least about 50%, at least about 60%, at least about 70%, at least about 80%, or at least about 90%.

The compounds of Formula (III) prepared from the formulations detailed above in section (I) have low levels of sulfate ions and bisulfate salts. For example, the compounds of Formula (III) comprise about 2700 ppm or less of sulfate ion and about 500 ppm or less of bisulfate salt.

(v) Applications

In embodiments in which $R^3$ is $C_1$ to $C_{12}$ alkyl, compounds of Formula (III) have solvent properties, i.e., can dissolve another substance or in which another substance can be dissolved. Accordingly, the compounds may be used as solvents in various applications and products including cleaning and personal care products, agricultural applications, industrial application, and coating or paint formulations.

In embodiments in which Z is SO and $R^3$ is $C_8$ to $C_{30}$ alkyl or alkenyl or $R^3$ is poly(ethylene oxide)alkyl, compounds of Formula (III) have surfactant properties. Compounds with surfactant properties may be used as detergents, cleaning agents, wetting agents, dispersing agents, emulsifying agents, foaming agents, or anti-foaming agents in numerous consumer/industrial products and/or applications.

(d) Alpha Ester Derivatives

In still other embodiments, the compounds of Formula (I) may undergo an esterification reaction such that the hydroxyl group at the alpha carbon is converted into an ester group. The process comprises contacting the formulation described above in section (I) with an acyl halide of formula $R^6C(O)Y$ to convert compounds of Formula (I) to compounds of Formula (IV):

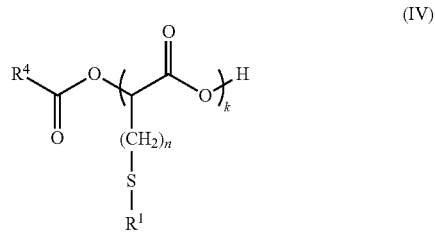

wherein $R^1$, k, and n are as defined above in section (I)(a), $R^4$ is aliphatic or substituted aliphatic, and Y is a halide ion.

(i) Acyl Halide

In certain embodiments, $R^4$ may be alkyl, substituted alkyl, alkenyl, substituted alkenyl, alkynyl, or substituted alkynyl. In some embodiments, $R^4$ may be $C_1$ to $C_{30}$ alkyl, substituted $C_1$ to $C_{30}$ alkyl, $C_2$ to $C_{30}$ alkenyl, or substituted $C_2$ to $C_{30}$ alkenyl. The alkyl and alkenyl groups may be linear, branched, or cyclic, and the alkenyl groups may contain from one to six carbon-carbon double bonds. In some embodiments, $R^4$ may be $C_6$ to $C_{24}$ alkyl or $C_6$ to $C_{24}$ alkenyl. In specific embodiments, $R^4$ may be $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl or alkenyl. The halide ion (Y) of the acyl halide may be chloride, bromide, fluoride, or iodide.

The acyl halide may be derived from a natural fatty acid (the natural fatty acid may be linear, branched, saturated, or unsaturated). Non-limiting examples of suitable acyl halides include hexanoyl halide, heptanoyl halide, octanoyl halide, nonanoyl halide, undecanoyl halide, dodecanoyl (lauroyl) halide, tridecanoyl halide, tetradecanoyl (myristoyl) halide, pentadecanoyl halide, hexadecanoyl (palmitoyl) halide, heptadecanoyl halide, octadecanoyl (stearoyl) halide, nonadecyoyl halide, arachidoyl halide, behenoyl halide, lignoceroyl halide, crotoyl halide, myristoloyl halide, palmitoloyl halide, sapienoyl halide, oloyl halide, elaidoyl halide, vaccenoyl halide, linoloyl halide, linoelaidoyl halide, linolenoyl halide, arachidonoyl halide, eicosapentaenoyl halide, erucoyl halide, and docosahexaenoyl halide.

The amount of acyl halide contacted with the compounds of Formula (I) can and will vary. In general, the mole-to-mole ratio of the compounds of Formula (I) to the acyl halide, $R^2C(O)Y$, may range from about 1:0.2 to about 1:2.0. In some embodiments, the mole-to-mole ratio of the compounds of Formula (I) to the acyl halide may range from about 1:0.3 to about 1:1.5, from about 1:0.4 to about 1:1.2, or from about 1:0.5 to about 1:1.0.

(ii) Optional Catalyst and Proton Acceptor

The esterification reaction may be conducted in the presence of a catalyst and a proton acceptor. In specific embodiments, the catalyst may be a nucleophilic catalyst. Non-limiting examples of suitable nucleophilic catalysts include 4-dimethylaminopyridine (DMAP), pyridine or derivatives thereof, imidazole or derivatives thereof, amidines, isothioureas, and guanidines. In a specific embodiment, the nucleophilic catalyst may be DMAP. Typically, a catalytic amount of the catalyst is used in the process.

Suitable proton acceptors include, without limit, organic bases such as triethylamine, diisopropylethylamine, N-methylmorpholine, and mixtures thereof; organic buffers (for example, 4-(2-hydroxyethyl)piperazine-1-ethanesulfonic acid (HEPES), 2 (4 morpholinyl) ethanesulfonic acid (MES), 4-morpholinepropanesulfonic acid (MOPS), 1,4-piperazinediethanesulfonic acid (PIPES), salts and/or mixtures thereof); borate salts; di- and tri-basic phosphate salts; bicarbonate salts; hydroxide salts; carbonate salts, or mixtures thereof. In general, the mole-to-mole ratio of the compounds of Formula (I) to the proton acceptor ranges from about 1:0.1 to about 1:10. In various embodiments, the mole-to-mole ratio of the compounds of Formula (I) to the proton acceptor may range from range from about 1:0.5 to about 1:5, from about 1:1 to about 1:4, or from about 1:1.8 to about 1:2.2.

(iii) Optional Solvent

The reaction may be conducted neat or in the presence of a solvent. The solvent may be a nonpolar solvent, a protic polar solvent, an aprotic polar solvent, or a combination thereof. Non-limiting examples of suitable nonpolar solvents include benzene, butyl acetate, tert-butyl methyl ether, chlorobenzene, chloroform, chloromethane, cyclohexane, dichloromethane (DCM), dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Suitable protic polar solvents include without limit amides such as formamide, acetamide, and the like. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In specific embodiments, the solvent may be dichloromethane (DCM).

The volume-to-mass ratio of the solvent to the compounds of Formula (I) can and will vary. Typically, the volume-to-mass ratio of the solvent to the compounds of Formula (I) may range from about 1:1 to about 100:1. In various embodiments, the volume-to-mass ratio of the solvent to the compounds of Formula (I) may range from about 1:1 to about 3:1, from about 3:1 to about 10:1, from about 10:1 to about 30:1, or from about 30:1 to about 100:1. In preferred embodiments, the volume-to-mass ratio of the solvent to the compounds of Formula (I) may range from about 10:1 to about 30:1.

(iv) Reaction Conditions

The reaction may be conducted at a temperature that ranges from about −10° C. to about 80° C. In certain embodiments, the temperature of the reaction may range from about 0° C. to about 20° C., from about 40° C. to about 40° C., from about 40° C. to about 60° C., or from about 60° C. to about 80° C. In specific embodiments, the reaction may be initiated at about 0° C. and then the temperature may be increased to about room temperature. In general, the reaction will be conducted at atmospheric pressure.

The duration of the reaction can and will vary. In general, the reaction may be allowed to proceed from about 1 hour to about 24 hours or more. In some embodiments, the reaction may be allowed to proceed overnight (or from about 12 to about 18 hours). Typically, however, the reaction is allowed to proceed for a sufficient period of time until the reaction has proceeded to the desired degree of completion, as determined by means well known to those of skill in the art. In embodiments in which the reaction is allowed to go to completion, a "completed reaction" generally means that the final reaction mixture contains a significantly diminished amount of the compounds of Formula (I) and a significantly increased amount of the compounds of Formula (IV) compared to the amounts of each present at the beginning of the reaction.

The compounds of Formula (IV) may be isolated from the reaction mixture by means known in the art. Suitable means include extracting, washing, precipitating, filtering, distilling, evaporating, drying, chromatography, and combinations thereof. Compounds of Formula (IV) may comprise monomers, dimers, trimers, and/or longer oligomers. In some embodiments, individual monomers, dimers, etc. may be isolated.

The yield of the compounds of Formula (IV) can and will vary. In general, the yield of the compound may be at least about 20%, at least about 30%, at least about 40%, at least about 50%, at least about 60%, at least about 70%, at least about 80%, or at least about 90%.

The compounds of Formula (IV) prepared from the formulation detailed above in section (I) has low levels of sulfate ions and bisulfate salts. For example, the compounds of Formula (IV) comprise about 2700 ppm or less of sulfate ion and about 500 ppm or less of bisulfate salt.

(v) Preparation of Carboxylates of the Compound of Formula (IV)

In some embodiments, the compound of Formula (IV) may be contacted with a salt to form a carboxylate in which a cation is complexed with the deprotonated hydroxyl of the carboxyl group. Examples of suitable cations include ammonium and metals such as sodium, potassium, lithium, cesium, magnesium, calcium, manganese, cobalt, nickel, copper, zinc, and iron. Suitable salts include, without limit, hydroxides, oxides, carbonates, bicarbonates, and the like. In some embodiments, the salt is free (e.g., is in solution). In other embodiments, the salt is bound to a resin (e.g., an ion exchange resin).

The amount of salt contacted with the compounds of Formula (IV) can and will vary. In general, the mole-to-mole ratio of the compounds of Formula (IV) to the salt may range from about 1:0.5 to about 1:2. In specific embodiments, the mole-to-mole ratio of the compounds of Formula (IV) to the salt may be about 1:1.

The reaction may be performed in the presence of a solvent. Suitable solvents and ratios are detailed above. The reaction may proceed under homogenous or heterogeneous reaction conditions. The temperature of the reaction may vary, but generally ranges from about 10° C. to about 50° C. The duration of the reaction may vary, but generally ranges from about one hour to about one day. In general, the reaction is allowed to proceed until the reaction is complete or substantially complete, as determined by means well known to those of skill in the art.

(vi) Applications

In embodiments in which $R^4$ is $C_6$ to $C_{24}$ alkyl or $C_6$ to $C_{24}$ alkenyl, compounds of Formula (IV) or carboxylates thereof have surfactant properties, and may be used as detergents, cleaning agents, wetting agents, dispersing agents, emulsifying agents, foaming agents, anti-foaming agents, or antimicrobial agents in numerous consumer/industrial products and/or applications.

(e) Diester Derivatives

In additional embodiments, the compounds of Formula (I) may undergo two esterification reactions to form diester derivatives. The process comprises contacting the formulation described above in section (I) with $R^3OH$ to form an ester, and contacting the ester with $R^4C(O)Y$ to form a diester of Formula (V):

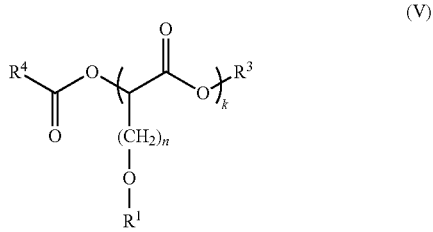

wherein $R^1$, k, and n are as defined above in section (I)(a), $R^3$ is as defined above in section (IV)(c), and $R^4$ and Y are as defined above in section (IV)(d).

The first esterification reaction is essentially as described above in section (IV)(c). The second esterification reaction is essentially as described above in section (IV)(d). Compounds of Formula (V) may comprise monomers, dimers, trimers, and/or longer oligomers.

The compounds of Formula (V) prepared from the formulation detailed above in section (I) have low levels of sulfate ions and bisulfate salts. For example, the compounds of Formula (V) comprise about 2700 ppm or less of sulfate ion and about 500 ppm or less of bisulfate salt.

The diester compounds of Formula (V) have plasticization properties and can be used to improve the flexibility and/or impact properties of a polymer. In some embodiments, the diester compounds of Formula (V) may have surfactant properties. Accordingly, such compound may be used as detergents, cleaning agents, wetting agents, dispersing agents, emulsifying agents, foaming agents, or antifoaming agents in numerous consumer/industrial products and/or applications.

(f) Polymers of Compounds of Formula (I)

In further embodiments, compounds of Formula (I) may undergo polymerization reactions to form polymers having repeat units of Formula (VI). The process comprises comprising contacting the formulation described above in section (I) with an acid catalyst under dehydration condition to form a mixture; and subjecting the mixture to reduced pressure and increased temperature to form polymers in which the average number of repeat units of Formula (VI) is greater than k in the starting formulation. The repeat unit of Formula (VI):

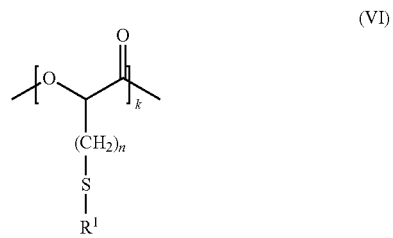

wherein $R^1$ and n are as defined above in section (I)(a).

(i) Acid Catalyst

The aid catalyst used in the process can and will vary and may be chosen from catalysts known in the art. In some embodiments, the acid catalyst may be chosen from organic acids, inorganic acids, or solid resins. Exemplary acid catalysts include, without limitation, boric acid, hydrochloric acid, trifluoroacetic acid, methanesulfonic acid, ortho- meta- and para-toluenesulfonic acid, sulfuric acid, phosphoric acid, tosylic acid, xylenesulfonic acid, Dowex resins, Amberlyst resins, Zn dust, and Sn based catalysts (such as, for example, Sn dust, tin oxide, tin (II) chloride, dibutyltin dilaurate, and stannous octoate), germanium dioxide, antimony trioxide, zinc oxide, iron (III) oxide, aluminum oxide, silicon dioxide, titanium dioxide, mixtures, and combinations thereof. In specific embodiments, the acid catalyst may be stannous octoate.

The acid catalyst may be added in a range of ratios to the compounds of Formula (I). In some aspects, the amount of catalyst added may range from about 0.01 wt % to about 1 wt % or higher of the compounds of Formula (I). In some embodiments, the acid catalyst may be added in an amount ranging from about 0.1 wt % to about 0.5 wt % of the compounds of Formula (I). In still other embodiments, the acid catalyst is added in an amount of about 0.1 wt %, 0.2 wt %, 0.3 wt %, 0.4 wt %, or 0.5 wt % the compounds of Formula (I).

(ii) Optional Solvent

The process may be carried out in the presence of a solvent, or may be conducted in the absence of solvent. The solvent may be a nonpolar solvent, a protic polar solvent, an aprotic polar solvent, or a combination thereof. Non-limiting examples of suitable nonpolar solvents include anisole, benzene, butyl acetate, tert-butyl methyl ether, chlorobenzene, chloroform, chloromethane, cyclohexane, dichloromethane, dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, xylene and combinations thereof. Examples of suitable protic polar solvents include without limit water, alcohols (e.g., methanol, ethanol, isopropanol, n-propanol, isobutanol, n-butanol, s-butanol, t-butanol), diols (e.g., propylene glycol and the like), organic acids (e.g., formic acid, acetic acid, and so forth), amides (e.g., formamide, acetamide, and the like), and combinations of any of the above. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2- dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In another embodiment, the solvent may be an azeotropic distillation solvent. In specific embodiments, the solvent may anisole, toluene, or xylene.

The weight-to-weight ratio of the solvent to the compounds of Formula (I) can and will vary. Typically, the weight-to-weight ratio of the solvent to the compounds of Formula (I) may range from about 1:1 to about 20:1. In various embodiments, the weight-to-weight ratio of the solvent to the compounds of Formula (I) may be about 2:1, 3:1, 3.5:1, 4.0:1, 4.5:1, 5.0:1, 5.5:1, 6.0:1, 6.5:1. 7.0:1, 7.5:1, 8:1, 8:1, or 10:1.

(iii) Optional Agents

In some embodiments, the reaction mixture may be supplemented with at least one additional monomer such that a copolymer is produced. Non-limiting examples of suitable monomers include diacids, diols, hydroxyl acids, acrylates, aminoacrylates, alkylene succinates, alkylene oxalates, anhydrides, arylates, carbonates, celluloses, caprolactones, cyanoacrylates, cyclic ethers, dihydropyrans, dioxanes, dioxanones, ether ether ketones, ethylene glycols, esters, fumarates, hydroxyl alkanoates, hydroxy esters, imides, ketals, lactides, lactones, methacrylates, methyl olefins, orthoesters, phosphazines, styrenes, terephthalates, tetrahydrofurans, trimethylene carbonates, urethanes, vinyl acetates, vinyl ketones, vinyl halides, derivatives of any of the forgoing, or mixtures thereof.

The weight ratio of the compounds of Formula (I) to the additional monomer(s) may vary depending on the desired properties of the copolymer. In some aspects, the weight ratio of the compounds of Formula (I) to the additional monomer(s) may range from about 99.9:0.1 to about 0.1:99.9. In various embodiments the weight ratio of the compounds of Formula (I) to the additional monomer (s) may be about 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99 weight %.

In other embodiments, a chain extender may be added to the reaction mixture. Chain extenders may be chosen from those known in the art. Suitable chain extenders include, without limitation, adipic acid, succinic acid, citric acid, isocyanates, such as 1,6-hexamethylene diisocyanate, oxazoline extenders, such as 2,2-bis(2-oxazoline) succinic anhydride and polyethene glycols (PEG). In some embodiments, the chain extender may be added in an amount ranging from about 0.01 wt % to about 10 wt % to the compounds of Formula (I).

(iv) Reaction Conditions—First Step of the Process

The reaction mixture is subjected dehydration to promote formation of the polymer. In certain embodiments, dehydration may be accomplished via distillation. For example, the reaction mixture may be subjected to simple distillation, fractional distillation, azeotropic distillation, azeotropic distillation using a Dean Stark or another similar trap, steam distillation, vacuum distillation, distillation using a Dean Stark trap or another similar trap, and the like. In one embodiment, the reaction mixture is subjected azeotropic distillation.

The first step of the process may be conducted at a temperature ranging from about 100° C. to about 200° C. In some aspects, the first step may be conducted at a temperature of about 100° C., 110° C., 120° C., 130° C., 140° C., 150° C., 160° C., 170° C., 180° C., 190° C., 200° C., or at a range between and including any two of these values. In specific embodiments, the temperature may be maintained at about 120° C. to about 150° C. throughout this step of the process.

In general, this step of the process is conducted under reduced pressure. In some embodiments, the pressure may be reduced to a pressure of about 100 mmHg to about 300 mmHg. In other embodiments, the pressure may be reduced to about 200 mmHg. In alternate embodiments, the process may commence at atmospheric pressure (i.e., 760 mmHg) and then the pressure may be reduced after a period of time. In further embodiments, this step of the process may be conducted under an inert atmosphere, such in an atmosphere of argon or nitrogen.

The duration of this step of the process can and will vary. In general, the first step may be allowed to proceed from about 2 hours to about 20 hours. In some aspects, the progress of the reaction may be monitored by measuring the amount of water removed during the process.

(v) Reaction Conditions—Second Step of the Process

The second step of the process comprises subjecting the reaction mixture to increased temperature and reduced pressure to form the polymers comprising the repeat unit of Formula (VI).

In various embodiments, this step of the process may be carried out at a temperature ranging from about 140° C. to about 250° C. In other embodiments, the reaction may be conducted at a temperature of about 140° C., 150° C., 160° C., 170° C., 180° C., 190° C., 200° C., 210° C., 220° C., 230° C., 240° C., 250° C., or at a range between and including any two of these values. In specific embodiments, the temperature may be about 170° C.

In some embodiments, the pressure may be maintained near the pressure of the first step and may range from about 100 mmHg to about 300 mmHg. In other embodiments, the pressure may be reduced to 0 mmHg to about 50 mmHg. In still other embodiments, the pressure may be reduced to about 0 mmHg, 10 mmHg, 20 mmHg, 30 mmHg, 40 mmHg, or 50 mmHg. In specific embodiments, the pressure may be reduced to about 30 mmHg. In some embodiments, the second step of the process may be conducted under dehydration conditions similar to those described in the first step.

The duration of the second step can and will vary. In general, the reaction may be allowed to proceed from about 2 hours to about 10 hours, or more preferably from about 3 hours to about 5 hours. Typically, however, the reaction is allowed to proceed for a sufficient period of time until the reaction is complete, as determined by means well known to those of skill in the art. In this context, a "completed reaction" generally means that the final reaction mixture contains a significantly diminished amount the compounds of Formula (I) and a significantly increased amount of the polymer comprising repeat units of Formula (IV) compared to the amounts of each present at the beginning of the reaction. In some aspects, the reaction completeness can be measured by monitoring the amount of water removed in the process and comparing to the theoretical amount of water.

The yield of the polymer produced by this process may be least about 30%, at least about 40%, at least about 50%, at least about 60%, at least about 70%, at least about 80%, or at least about 90%. In some embodiments, the resulting homopolymer or copolymer may have a low content of free monomers or dimers. The percentage of free monomer and dimer may range from about 0% to about 40% of the total homopolymer or copolymer produced. In some embodiments, the free monomer and dimer may comprise less than 30% of the total composition, or less than 20% of the total composition, or less than 10% of the total composition. In some embodiments, the percent free monomer may be less than about 10%, less than about 9%, less than about 8%, less than about 7%, less than about 6%, less than about 5%, less than about 4%, less than about 3%, less than about 2%, or less than about 1%.

The polymers comprising the repeat unit of Formula (VI) prepared from the formulations detailed above in section (I) have low levels of sulfate ions and bisulfate salts. For example, said polymers comprise about 2700 ppm or less of sulfate ion by weight and about 500 ppm or less of bisulfate salt.

The polymer may be used as is or the polymer optionally may be purified by means including by size exclusion chromatography (SEC), high performance liquid chromatography (HPLC), ion-exchange chromatography, other types of chromatography, precipitation, or crystallization.

The average molecular weight of the polymer can and will vary depending upon the reactants and the reaction conditions. In general, the polymer may have an average molecular weight from about several hundred up to about tens of thousands.

(vi) Applications

The polymers (or copolymers) comprising repeat units of Formula (VI) have a variety of uses in industrial or agricultural applications. Advantageously, these polymers are biodegradable and biocompatible.

(g) Sulfoxide or Sulfone Derivatives

Any of the compounds detailed above may undergo one or more oxidation reactions to convert the sulfur into a sulfoxide or a sulfone.

A variety of oxidizing agents may be used in this process. Non-limiting examples of suitable oxidizing agents include peroxy acids (e.g., chloroperoxybenzoic acid, peracetic acid, peroxysulfuric acid), hydrogen peroxide, perchlorates, chlorite, hypochlorite, chlorate, sulfuric acid, persulfuric acid, hexavalent chromium compounds, permanganate compounds, sodium perborate, nitric acids, nitrate compounds, metal oxidants (such as, e.g., benzeneselenic acid, lead tetraacetate, osmium tetroxide, phosphomolybdic acid hydrate, pyridinium chlorochromate, pyridinium dichromate, quinolinium dichromate, and the like). and combinations thereof. In preferred embodiment, the oxidizing agent may be m-chloroperoxybenzoic acid or hydrogen peroxide.

The mole-to-mole ratio of the compound(s) of Formula (I), (II), (Ill), (IV), (V), or (VI) to the oxidizing agent can and will vary. In general, the mole-to-mole ratio of the compound to the oxidizing agent may range from about 1:0.1 to about 1:20, from about 1:0.2 to about 1:10, from about 1:0.5 to about 1:5, or from about 1:1 to about 1:3.

The oxidation reaction may be performed in the presence of a solvent. The solvent may be a nonpolar solvent, a protic solvent, or an aprotic solvent depending upon the nature of the reactants. Suitable solvents are detailed above. The volume-to-mass ratio of the solvent to the compound of Formula (I), (II), (Ill), (IV), (V), or (VI) can and will vary. Typically, the volume-to-mass ratio of the solvent to the compound may range from about 1:1 to about 60:1. In various embodiments, the volume-to-mass ratio of the solvent to the compound may range from about 4:1 to about 40:1.

The oxidation reaction may be conducted at a temperature that ranges from about −10° C. to about 50° C. In certain embodiments, the temperature of the reaction maybe about 0° C., about 10° C., about 20° C., about 25° C., or about 30° C. In one embodiment, the reaction may be allowed to proceed at about 0° C. In another embodiment, the reaction may be allowed to proceed for a first period of time at 0° C. and a second period of time at room temperature. In still another embodiment, the reaction may be conducted at room temperature. Typically, the reaction will be conducted at atmospheric pressure.

The duration of the reaction can and will vary. In general, the reaction may be allowed to proceed from several hours to several days. Typically, however, the reaction may be allowed to proceed for a sufficient period of time until the reaction is complete or substantially complete, as determined by means well known to those of skill in the art.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or R'S—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

As used herein, the term "aliphatic" refers to a hydrocarbyl group in which the carbon atoms are linked in open chains, i.e., either linear or branched but not cyclic. Alkyl, alkenyl, and alkynyl groups, optionally substituted, are aliphatic.

The term "alkyl" as used herein describes groups containing from one to thirty carbon atoms in the principal chain. They may be straight or branched chain or cyclic and include methyl, ethyl, propyl, isopropyl, butyl, hexyl and the like.

The term "alkenyl" as used herein describes groups containing from two to thirty carbon atoms in the principal chain and further comprising at least one carbon-carbon double bond. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups containing from two to thirty carbon atoms in the principal chain and further comprising at least one carbon-carbon triple bond. They may be straight or branched chain and include ethynyl, propynyl, butynyl, isobutynyl, hexynyl, and the like.

The term "amide" as used herein describes a compound comprising a carbonyl-nitrogen linkage.

The term "aminoacyl" refers to an amino acid residue.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The term "aryl" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

As used herein, the term "color bodies" refers to visible color or colored impurities that can be quantified by the use of a spectrophotometric colorimeter in the range of visible light, using wavelengths of approximately 400-700 nm.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, piperidyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. They may be straight, branched, or cyclic.

The term "protecting group" as used herein denotes a group capable of protecting a functional group (e.g., an alcohol or an amine), wherein the protecting group may be removed, subsequent to the reaction for which protection is employed, without disturbing the remainder of the molecule. Non-limiting examples of suitable alcohol protecting groups include acetyl (Ac), benzoyl (Bz), benzyl (Bn, Bnl), β-methoxyethoxymethyl ether (MEM), dimethoxytrityl (DMT), methoxymethyl ether (MOM), methoxytrityl (MMT), p-methoxybenzyl ether (PMB), methylthiomethyl ether, pivaloyl (Piv), tetrahydropyranyl (THP), trityl (triphenylmethyl, Tr), silyl ethers (e.g., trimethylsilyl (TMS), tert-butyldimethylsilyl (TBDMS), tri-iso-propylsilyloxymethyl (TOM), and triisopropylsilyl (TIPS) ethers), methyl ethers, and ethoxyethyl ethers (EE) and the like. Suitable amine protecting groups include without limit carbobenzyloxy (Cbz); p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts), and other sulfonamides (e.g., Nosyl & Nps), and the like. A variety of protecting groups and the synthesis thereof may be found in "Protective Groups in Organic Synthesis" by T. W. Greene and P. G. M. Wuts, John Wiley & Sons, 2006.

As used herein, the term "salt impurities" refers to bisulfate salts, sulfate and other anions, and/or ammonium and other cations.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

The following examples illustrate various embodiments of the present disclosure.

Example 1: Preparation of High Purity HMTBA Sample

Preparation of a high purity HMTBA to be used as starting material and control was achieved by hydrolyzing the cyclic dimer of HMTBA in water at 80° C., as shown in the reaction scheme below:

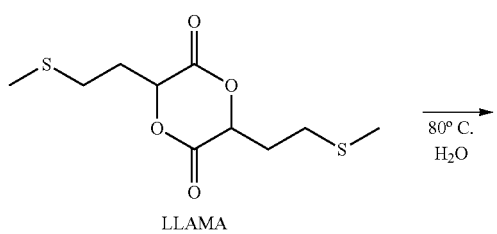

LLAMA

43

-continued

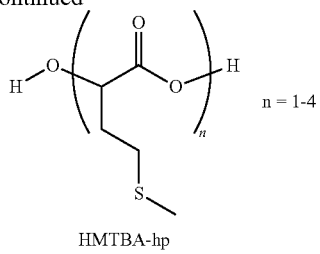

HMTBA-hp n = 1-4

The water in the reaction mixture was removed until the water concentration was approximately 11%. The resulting HMTBA product (HMTBA-hp) was shown to contain monomer, dimer, trimer, and small amounts of tetramer (n=1-4) by HPLC. The area % distribution at 210 nm for each component is shown in Table 1.

TABLE 1

HMTBA oligomer composition of HMTBA-hp.

| Sample | Monomer n = 1 (Area %) | Dimer n = 2 (Area %) | Trimer n = 3 (Area %) | Tetramer n = 4 (Area %) | Pentamer n = 5 (Area %) | n ≥ 5 (Area %) |
|---|---|---|---|---|---|---|
| 1 | 82.33 | 16.94 | 0.64 | 0.1 | 0 | 0 |

Further analysis revealed that the resulting HMTBA-hp contained 35 ppm of sulfate ion and an APHA value of 54. This formulation was used as the starting material to study the effects of various sulfate and bisulfate concentrations at elevated temperature.

Higher temperature is known to cause darkening in HMTBA formulations, in addition of increasing oligomer content. Examples 2 and 3 examine the effects of increasing concentrations of sulfuric acid or ammonium bisulfate on the color of the resulting HMTBA formulations during heating and oligomerization at 140° C. \. These examples provide accelerated tests to assess the color and odor stability of the HMTBA formulations.

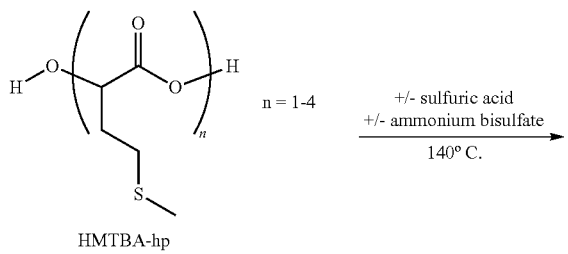

HMTBA-hp

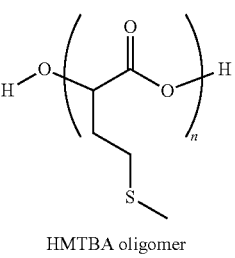

HMTBA oligomer

44

Example 2: Effect of Sulfuric Acid Concentration on the Color of HMTBA Formulations Approximately 22.5-30.5 grams of HMTBA-hp was weighed into 40 ml clear glass vials equipped with stir bars. A measured amount of a sulfuric acid solution (9.8 wt/wt %) was added to each vial to achieve the desired sulfate level as shown in Table 2. Aliquots (0.3 grams) were taken and diluted with deionized water (1.7 grams) and the pH of each (15%) solution was measured at room temperature using a pH meter. An aliquot (6.5 g) of each of the five solutions was dissolved in tetrahydrofuran (6.5 g) to prepare a 50 wt % solution and the APHA color value was measured by standard ASTM method D1209 with a Lovibond PFXi 195 Series instrument. Each sample was measured in triplicate and the average values are reported in Table 2.

Vials were capped with a septum and heated to 140° C. while being stirred at 500 rpm under nitrogen in a Chemglass PieBlock reactor station. Elapsed time was measured after the solutions reached 140° C. After 12 hours at 140° C., vials were quickly cooled to ambient temperature. An aliquot (6.5 g) of each of the five reactions was dissolved in tetrahydrofuran (6.5 g) to prepare a 50 wt % solution and the APHA color analysis was conducted as detailed above. The remaining samples were transferred from the vials into tared 20 mL glass headspace vials and were heated to 140° C. and stirred at 500 rpm for an additional 12 hours under nitrogen. Samples were then quickly cooled down to ambient temperature and the APHA color of each sample was determined by described above. The changes in APHA color values over time are shown in Table 2 and FIG. 1. The APHA color values of both samples 1 (i.e., HMTBA-hp) and sample 2 (i.e., HMTBA-hp with 0.1% of sulfuric acid) remained low even after heating at 140° C. for 24 hours.

TABLE 2

Effect of sulfuric acid addition on pH and color of HMTBA formulations vs. time at 140° C.

| | Sulfate | pH | 50% HMTBA solution in THF | | |
|---|---|---|---|---|---|
| Sample | Added (wt %) | (15% solution) | APHA value t = 0 | APHA value t = 12 | APHA value t = 24 |
| 1 | 0 | 1.56 | 54 | 100 | 103 |
| 2 | 0.1 | 1.56 | 51 | 114 | 125 |
| 3 | 0.27 | 1.57 | 50 | 176 | 377 |
| 4 | 0.39 | 1.57 | 49 | >500 | >500 |
| 5 | 0.72 | 1.48 | 48 | >500 | >500 |

The oligomeric composition of the samples after heating for 24 hours was analyzed by HPLC. The area % distribution for each component at 210 nm is reported in Table 3.

TABLE 3

HMTBA oligomer composition of samples with added sulfuric acid after 24 hours at 140° C.

| Sample | Monomer n = 1 (Area %) | Dimer n = 2 (Area %) | Trimer n = 3 (Area %) | Tetramer n = 4 (Area %) | Pentamer n = 5 (Area %) | n ≥ 5 (Area %) |
|---|---|---|---|---|---|---|
| 1 | 8.26 | 11.58 | 12.39 | 12.81 | 11.52 | 43.44 |
| 2 | 7.18 | 10.12 | 11.20 | 11.82 | 11.15 | 48.54 |
| 3 | 6.67 | 9.54 | 10.49 | 11.15 | 10.12 | 52.07 |
| 4 | 3.03 | 4.39 | 5.08 | 6.18 | 5.87 | 75.45 |
| 5 | 2.53 | 3.56 | 3.84 | 4.64 | 4.67 | 80.78 |

In conclusion, sulfuric acid concentration of equal to or less than 0.1% (measured as sulfate) did not result in a significantly colored (APHA <250) HMTBA formulations after 24 hours at 140° C. A sulfate concentration of greater than 0.27% resulted in dark colored HMTBA formulations (APHA >500). As expected all the HMTBA samples were extensively oligomerized (n>5) after heating (see Table 3). However, this example indicates that oligomerization itself does not adversely affect the sample color. The sample color was only affected by the amount of sulfuric acid present.

Example 3: Effect of Added Bisulfate Salt on the Color of HMTBA Formulations

Figure 2:
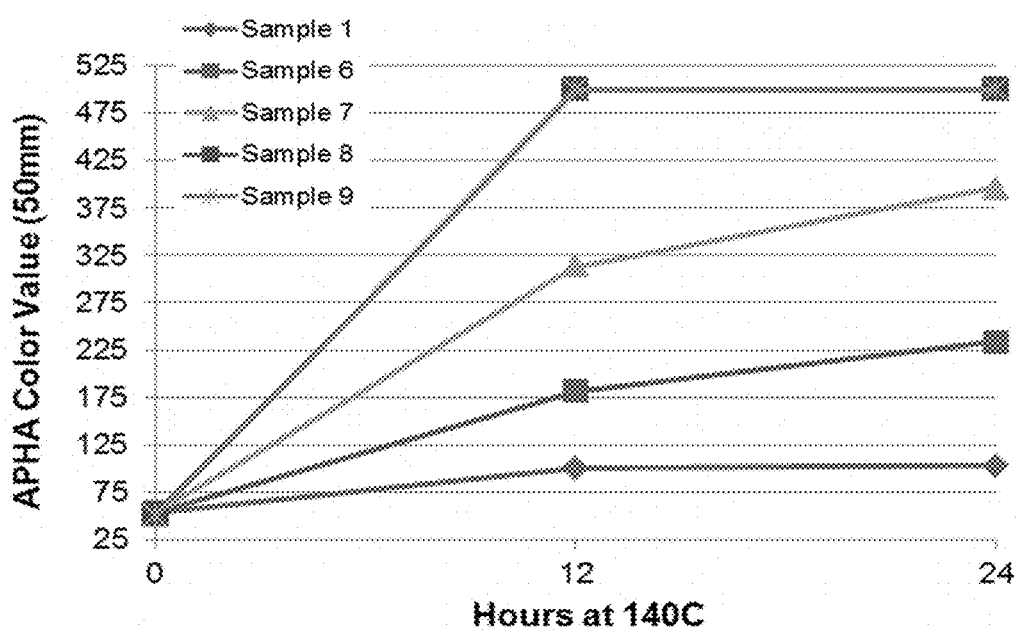
FIG. 2 shows APHA color value changes over time in HMTBA samples with added ammonium bisulfate and heated to 140° C. Plotted is the APHA color value as a function of hours at 140° C.

Approximately 22.5-30.5 grams of HMTBA-hp was weighed into five 40 ml clear glass vials equipped with stir bars. A solution of ammonium bisulfate (5 wt/wt %) was added to four of the samples to achieve the desired sulfate level (see Table 4). Aliquots (0.3 grams) were taken and diluted with deionized water (1.7 grams) and the pH of each solution was measured at room temperature using a pH meter. The initial APHA color value of each sample was determined by colorimetry, essentially as described in Example 2. The remaining samples were capped and heated to 140° C. with stirring at 500 rpm under nitrogen for 12 hours or 24 hours, and APHA color values were determined essentially as described above in Example 2. The color changes are shown in Table 4 and FIG. 2.

TABLE 4

Effect of ammonium bisulfate addition on pH and color of HMTBA formulations vs. time at 140° C.

| Sample | Sulfate Added (wt %) | pH (15% solution) | 50% HMTBA solution in THF | | |
|---|---|---|---|---|---|
| | | | APHA value t = 0 | APHA value t = 12 | APHA value t = 24 |
| 1 | 0 | 1.56 | 54 | 100 | 103 |
| 2 | 0.01 | 1.5 | 54 | 181 | 234 |
| 3 | 0.05 | 1.41 | 54 | 314 | 396 |
| 4 | 0.10 | 1.6 | 51 | >500 | >500 |
| 5 | 0.25 | 1.35 | 50 | >500 | >500 |

The oligomeric composition of the samples after heating for 24 hours was analyzed by HPLC. The area % distribution for each component at 210 nm was reported (see Table 5).

TABLE 5

HMTBA oligomer composition of samples with added ammonium sulfate after 24 hours at 140° C.

| Sample | Monomer n = 1 (Area %) | Dimer n = 2 (Area %) | Trimer n = 3 (Area %) | Tetramer n = 4 (Area %) | Pentamer n = 5 (Area %) | n ≥ 5 (Area %) |
|---|---|---|---|---|---|---|
| 1 | 8.26 | 11.58 | 12.39 | 12.81 | 11.52 | 43.44 |
| 6 | 3.69 | 5.68 | 6.92 | 8.41 | 8.10 | 67.21 |
| 7 | 5.12 | 7.20 | 7.90 | 9.01 | 8.39 | 62.38 |
| 8 | 5.32 | 7.43 | 7.99 | 8.60 | 8.37 | 62.29 |
| 9 | 5.61 | 7.60 | 8.16 | 8.60 | 8.40 | 61.63 |

In conclusion, a bisulfate concentration (from ammonium bisulfate) of equal to or less than 0.01% did not result in a significantly colored (APHA <250) HMTBA formulation after 24 hours at 140° C. Sulfate concentrations of greater than 0.27% resulted in dark colored HMTBA samples (APHA >500). Also the data shows that all the reaction mixtures were oligomerized (n>5) to the same extent. These data clearly indicate that oligomerization itself did not adversely affect sample color. The sample color was only affected by the amount of ammonium bisulfate present.

Example 4: Process to Produce Specialty HMTBA Products or Formulations from Commercial HMTBA Sources by Contact with an Adsorbent A decolorized formulation (HMTBA OP) was prepared from an HMTBA animal supplement (88% HMTBA) by dilution with water to provide an aqueous solution with the desired HMTBA concentration and passing the resulting solution through an activated charcoal column to remove color bodies (see process diagrammed in FIG. 3A). Water was removed from the decolorized solution to provide HMTBA OP. No bisulfate salt or sulfuric acid was removed by this process.

Example 5: Process to Produce Specialty HMTBA Products or Formulations from Commercial HMTBA Sources by Solvent Extraction A specialty HMTBA formulation (HMTBA P5) was prepared from an HMTBA animal supplement (88% HMTBA) using the solvent extraction process diagrammed in FIG. 3B. For this, HMTBA animal supplement was diluted with water to provide an aqueous solution with the desired HMTBA concentration and the resulting solution was passed through an activated charcoal column to remove colored bodies. The decolorized HMTBA solution was extracted with methyl isobutyl ketone (MIBK). For this, 1 g of HMTBA was contacted with 0.75 g of MIBK, and the phases were separated. The organic phase contained HMTBA while sulfuric acid and the bisulfate salts remained in the aqueous phase. MIBK was then distilled off the organic phase to provide the HMTBA P5 sample.

Example 6: Process to Produce Specialty HMTBA Products or Formulations from Commercial HMTBA Source by Ion Exchange Process A specialty HMTBA formulation (HMTBA IEX) was prepared from an HMTBA animal supplement (88% HMTBA) using the ion exchange process diagrammed in FIG. 3C. HMTBA animal supplement (88% HMTBA) was diluted with water to provide an aqueous solution with the desired HMTBA concentration and the resulting solution was passed through an activated charcoal column to remove colored bodies. The decolorized HMTBA solution was then passed through a strong acid cation exchange column followed by a weak base anion exchange resin and the final aqueous solution was concentrated to provide HMTBA IEX.

Table 6 shows a comparison of the HMTBA formulation obtained by the process described in Examples 4 and 5 and the starting HMTBA animal supplement

TABLE 6

Properties of various HMTBA formulations.

Figure 3A:
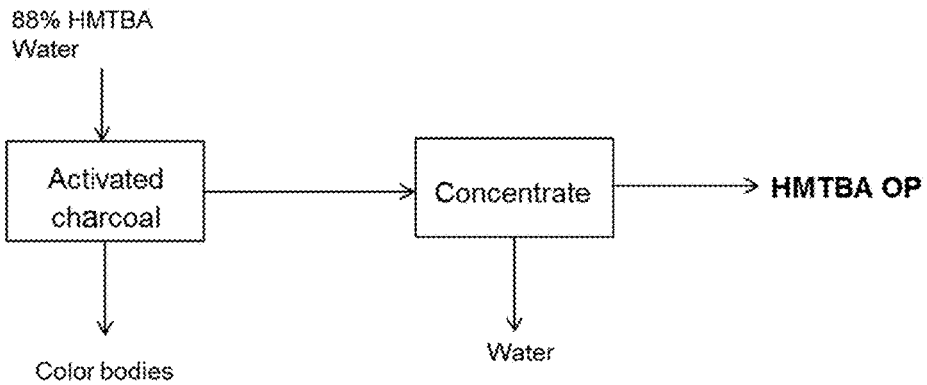
FIG. 3A diagrams a process from removing colored impurities (or color bodies) from HMTBA.
Figure 3B:
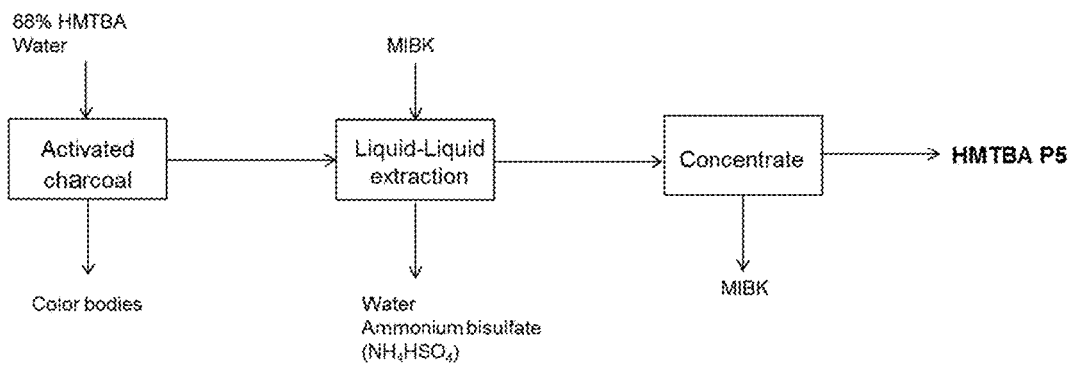
FIG. 3B presents a diagram of a solvent extraction process for preparing specialty HMTBA.
Figure 3C:
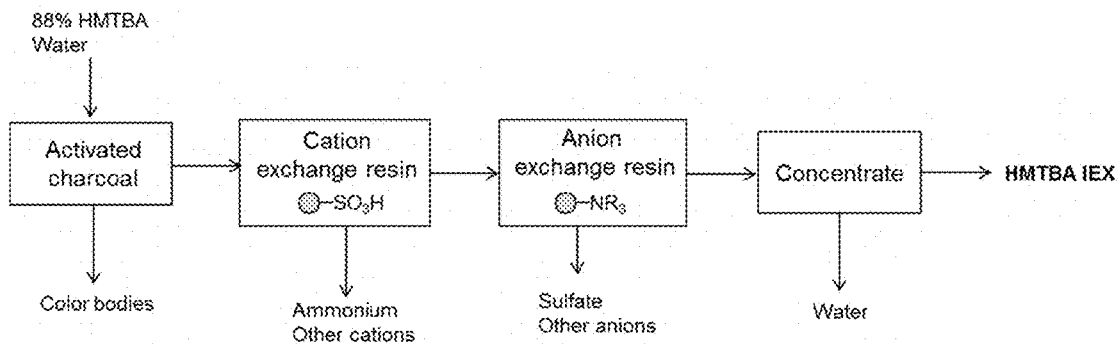
FIG. 3C shows a diagram of an ion exchange process for preparing specialty HMTBA.

| Formulation | Process Description | Sulfate Content | Water content | Color value |
|---|---|---|---|---|
| HMTBA animal supplement | — | 0.6% | ~12% | >500 (APHA) |
| HMTBA OP | FIG. 3A | 0.6% | 6.73% | 172 (APHA) |
| HMTBA P5 | FIG. 3B | 95 ppm (0.0095%) | 2.68% | 177 (APHA) |
| HMTBA IEX | FIG. 3C | 17 ppm (0.0017%) | 2.2% | 0.5 (Gardner) |

Example 7: Dilution and Filtration of Commercial HMTBA Source

HMTBA animal supplement (88% HMTBA) was diluted with water to provide an aqueous solution comprising 15% HMTBA. The aqueous solution of 15% HMTBA was mixed well and allowed to stand for 18-24 hours at room temperature. During this time oily color bodies form. The aqueous solution comprising the oily color bodies was filtered through CELITE® to remove the oily color bodies.

The filtered aqueous solution of 15% HMTBA can be contacted with activated charcoal, as described in Example 4, and further purified by solvent extraction, as described in Example 5 or ion exchange, as described in Example 6.

What is claimed is:

1. A formulation comprising a mixture of compounds of Formula (I), 15% or less by weight of water, and 2700 ppm or less by weight of sulfate ion, wherein k is 1 in less than 85% by weight of the mixture of compounds of Formula (I):

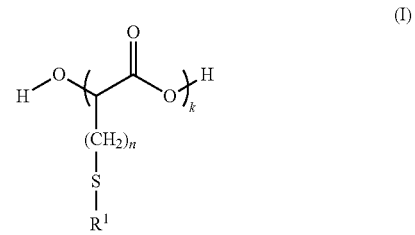

wherein:
R¹ is alkyl or substituted alkyl;
k is an integer from 1 to 1000; and
n is an integer from 1 to 20.

2. The formulation of claim 1, wherein R¹ is methyl, k is from 1 to 50 and n is 2.

3. The formulation of claim 1, which has an American Public Health Association (APHA) color value of 200 or less.

4. The formulation of claim 1, which has an APHA color value of 500 or less after heating at 140° C. for up to 12 hours.

5. The formulation of claim 1, which comprises 500 ppm or less by weight of bisulfate ion.

6. The formulation of claim 1, which comprises 15% by weight of water and has a pH value of at least 1.3.

7. A formulation comprising a mixture of compounds of Formula (I), 15% or less by weight of water, and having an American Public Health Association (APHA) color value of 200 or less, wherein k is 1 in less than 85% by weight of the mixture of compounds of Formula (I):

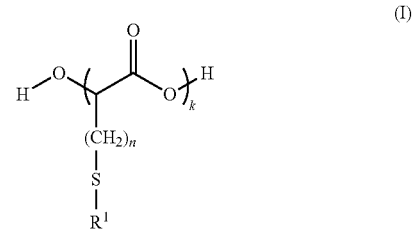

wherein:
R¹ is alkyl or substituted alkyl;
k is an integer from 1 to 1000; and
n is an integer from 1 to 20.

8. The formulation of claim 7, wherein R¹ is methyl, k is from 1 to 50 and n is 2.

9. The formulation of claim 7, wherein the APHA color value is 500 or less after heating at 140° C. for up to 12 hours.

10. The formulation of claim 7, which comprises 2700 ppm or less by weight of sulfate ion.

11. The formulation of claim 7, which comprises 500 ppm or less by weight of bisulfate ion.

12. The formulation of claim 7, which comprises 15% by weight of water and has a pH value of at least 1.3.

13. A nutritional composition comprising the formulation of claim 1 and at least one agent chosen from a nutritional agent, a bioactive agent, an excipient, or a combination thereof.

14. The nutritional composition of claim 13, wherein the nutritional agent is chosen from a carbohydrate source, a protein source, a lipid source, or a combination thereof, and the bioactive agent is chosen from a vitamin, a mineral, an amino acid, hydroxy analog of an amino acid, an antioxidant, an organic acid, a poly unsaturated fatty acid, an essential oil, an enzyme, a prebiotic, a probiotic, a herb, a pigment, a pharmaceutically active agent, or combinations thereof.

15. The nutritional composition of claim 13, which is a food composition, a nutritional supplement, a dietary supplement, a feed composition, a feed premix, a pet food, a pet food supplement, or a feline urinary tract health food.

16. An industrial composition comprising the formulation of claim 1 and at least one agent chosen from a solvent, a surfactant, a wetting agent, a polymer, a plasticizer, a binder, a filler, a thickening agent, a foam control agent, a dispersant, a disintegrant, a pH regulating agent, a chelating agent, a preservative, a pigment, a heat stabilizer, a UV/light stabilizer, a flame retardant, a biocide, a processing aid, a thermal modifier, an impact modifier, a blowing agent, a lubricant, a nucleating agent, or combinations thereof.

17. An agricultural composition comprising the formulation of claim 1 and at least one agent chosen from an herbicide, a fungicide, an insecticide, a fertilizer, a solvent, a surfactant, a binder, a filler, a wetting agent, a thickening agent, a foam control agent, a dispersant, a disintegrant, a pH regulating agent, a chelating agent, a preservative, a pigment, or combinations thereof.

18. A process for preparing the formulation of claim 1 from a feed grade formulation comprising a mixture of compounds of Formula (I), the feed grade formulation further comprising sulfate ions, bisulfate ions, and color bodies, the process comprising:
  (a) contacting an aqueous solution of the feed grade formulation comprising the mixture of compounds of Formula (I) with an adsorbent to remove color bodies, thereby producing a decolorized aqueous solution;
  (b1) extracting the decolorized aqueous solution from step (a) with a solvent having limited water miscibility to form an organic phase comprising the solvent having limited water miscibility and the mixture of compounds of Formula (I) and an aqueous phase comprising sulfate and bisulfate ions; and
  (c1) removing the solvent from the organic phase to prepare the formulation of claim 1;
  or
  (b2) contacting the decolorized aqueous solution from step (a) with at least one ion exchange resin to remove sulfate and bisulfate ions and form an aqueous elute; and
  (c2) removing water from the aqueous eluate to prepare the formulation of claim 1.

19. The process of claim 18, wherein the aqueous solution of the feed grade formulation comprising the mixture of compounds of Formula (I) comprises 18% or less by weight of the mixture of compounds of Formula (I).

20. The process of claim 18, wherein the aqueous solution of the feed grade formulation comprising the mixture of compounds of Formula (I) is filtered prior to contact with the adsorbent in step (a).

21. The process of claim 18, wherein the adsorbent is activated charcoal.

22. The process of claim 18, wherein the solvent having limited water miscibility used in step (b1) is benzene, n-butanol, butyl acetate, carbon tetrachloride, chlorobenzene, chloroform, chloromethane, cyclohexane, dichloromethane, 1,2-dichloroethane, di-tert-butyl ether, dimethyl ether, diethylene glycol, diethyl carbamate, diethyl ether, diglyme, diisopropyl ether, ethyl acetate, ethyl tert-butyl ether, ethylene oxide, fluorobenzene, heptane, hexane, methyl isobutyl ketone, methyl tert-butyl ether, pentane, trichloroethylene, toluene, xylene, or a combination thereof.

23. The process of claim 22, wherein the solvent having limited water miscibility is methyl isobutyl ketone, ethyl acetate, or methyl tert-butyl ether.

24. The process of claim 18, wherein the contacting at step (b2) comprises contact with a cation exchange resin followed by contact with an anion exchange resin, or the contacting at step (b2) comprises contact with an anion exchange resin followed by contact with a cation exchange resin.

* * * * *